United States Patent [19]
Jendralla et al.

[11] Patent Number: 5,294,724
[45] Date of Patent: Mar. 15, 1994

[54] 4-HYDROXYTETRAHYDROPYRAN-2-ONES AND THE CORRESPONDING DIHYDROXYCARBOXYLIC ACID DERIVATIVES, SALTS AND ESTERS AND A PROCESS FOR THEIR PREPARATION

[75] Inventors: Heiner Jendralla, Frankfurt am Main; Günther Wess, Erlensee; Kurt Kesseler, Bad Soden; Gerhard Beck, Frankfurt am Main, all of Fed. Rep. of Germany

[73] Assignee: Hoechst Aktiengesellschaft, Frankfurt am Main, Fed. Rep. of Germany

[21] Appl. No.: 578,240

[22] Filed: Sep. 6, 1990

[30] Foreign Application Priority Data

Sep. 8, 1989 [DE] Fed. Rep. of Germany ....... 3929913

[51] Int. Cl.$^5$ ................ C07D 309/30; C07C 69/612; C07C 321/04; C07C 321/26
[52] U.S. Cl. ..................... 549/292; 560/17; 560/60; 560/61; 560/62
[58] Field of Search ............ 549/292; 514/468; 560/17, 60, 61, 62

[56] References Cited

FOREIGN PATENT DOCUMENTS

| | | | |
|---|---|---|---|
| 0216127 | 4/1987 | European Pat. Off. | 549/292 |
| 0283217 | 9/1988 | European Pat. Off. | |
| 0341681 | 11/1989 | European Pat. Off. | 549/292 |
| 0414206 | 2/1991 | European Pat. Off. | |
| 3632893 | 4/1988 | Fed. Rep. of Germany | |
| 3632893A1 | 4/1988 | Fed. Rep. of Germany | |
| 3722809 | 1/1989 | Fed. Rep. of Germany | 549/292 |
| 3819999A1 | 12/1989 | Fed. Rep. of Germany | |

OTHER PUBLICATIONS

Carew, et al., "Antiatherogenic effect of probucol unrelated to its hypocholesterolemic effect: Evidence that antioxidants in vivo can selectively inhibit low density lipoprotecin degradation in macrophage-rich fatty streaks and slow the progression of atheroscerosis in the Watanabe heritable hyperlipidemic rabbit," Proc. Natl. Acad. Sci. USA, vol. 84, pp. 7725-7729 (1987).
Nestel et al., "Effects of Probucol on Low Density Lipoprotein Removal and High Density Lipoprotein Synthesis," Artheroscierosis, 38, pp. 203-209 (1981).
Eder, "A Symposium: New Developments in the Treatment of Hypercholesterolemia—Probucol," The American Journal of Cardiology, vol. 57, No. 16, pp. 1H-54H (1986).
Fogelman, et al., "Malondialdehyde alteration of low density lipoproteins leads to cholesteryl ester accumulation in human monocyte-macrophages," Proc. Natl. Acad. Sci., USA, vol. 77, No. 4, pp. 2214-2218 (1980).
Stokker, et al., "3-Hydroxy-3-methylglutaryl-coenzyme A Reductase Inhibitors. 1. Structural Modification of 5-Substituted 3,5-Dihydroxypentanoic Acids and Their Lactone Derivatives," J. Med. Chem 1985, vol. 28, pp. 347-358 (1985).

*Primary Examiner*—C. Warren Ivy
*Assistant Examiner*—A. A. Owens
*Attorney, Agent, or Firm*—Finnegan, Henderson, Farabow, Garrett & Dunner

[57] ABSTRACT

4-Hydroxytetrahydropyran-2-ones and the corresponding dihydroxycarboxylic acid derivatives, salts and esters, process for their preparation, their use as pharmaceuticals, and pharmaceutical preparations and precursors.

Compounds of the formula I

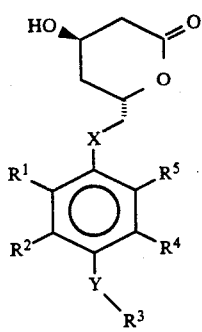

I (Abstract continued on next page.)

and the corresponding open-chain dihydroxycarboxylic acids of the formula II

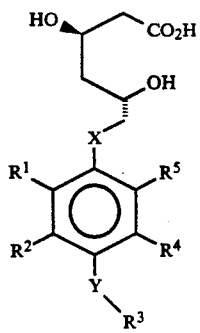

II in which X, Y, $R^1$, $R^2$, $R^3$, $R^4$ and $R^5$ have the meanings indicated, and also their pharmacologically tolerable salts with bases and their pharmacologically tolerable esters, processes for the preparation of these compounds, their use as pharmaceuticals and pharmaceutical preparations are described. In addition, compounds of the formula III

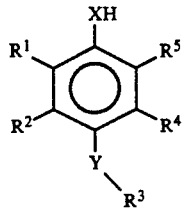

III in which $R^1$, $R^2$, $R^3$, $R^4$, $R^5$, X and Y have the meanings indicated are described.

3 Claims, No Drawings

4-HYDROXYTETRAHYDROPYRAN-2-ONES AND THE CORRESPONDING DIHYDROXYCARBOXYLIC ACID DERIVATIVES, SALTS AND ESTERS AND A PROCESS FOR THEIR PREPARATION

The enzyme 3-hydroxy-3-methylglutaryl-coenzyme A reductase (HMG-CoA reductase) plays a central role in the biosynthesis of cholesterol [A. Endo, J. Med. Chem. 28, 401 (1985) ]. Inhibitors of this enzyme, in particular mevinolin, synvinolin and eptastatin have been clinically tested for the treatment of hypercholesterolemics. Structurally simplified, fully synthetic analogs of these compounds have been described [T.-J. Lee, TIPS 8, 442 (1987) ]. For some time, an involvement of lipid peroxidation in the formation of arteriosclerotic lesions has also been discussed. Thus, it has been observed that oxidatively modified forms of low density lipoprotein (LDL) cause a great enrichment of cholesterol esters in macrophages [M. A. Fogelman et al., Proc. Natl. Acad. Sci. USA 77, 2214 (1980)] and additionally lead to increased release of a number of lysosomal enzymes and pathogenic mediators. Only recently, it was shown by the use of probucol that the suppression of LDL oxidation is more essential for the avoidance of atherosclerotic processes than its action on the serum cholesterol level [D. Steinberg et al., Proc. Natl. Acad. Sci. USA 84, 7725 (1987)].

In human medicine, probucol of the formula

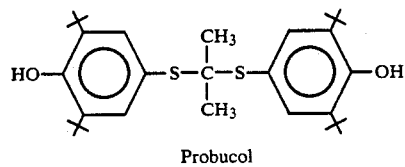

Probucol is used for the treatment of hyperlipoproteinemia.

According to an incompletely researched mechanism, probucol lowers both LDL and HDL. Probucol increases the rate of catabolism of LDL [P. J. Nestel, T. Billington, Atherosclerosis 38, 203 (1981) ] and increases biliary cholesterol excretion. Compared with a potent cholesterol biosynthesis inhibitor (such as mevinolin), however, the plasma cholesterol-lowering action of probucol is only poorly pronounced. Recently, the therapeutic use of probucol has principally been traced back to the fact that probucol in vivo prevents oxidative modification of LDL [Symposium: New Developments in the Treatment of Hypercholesterolemia—Probucol, various authors, Am. J. Cardiol. 57, 1H-54H (1986)].

The antioxidative and radical entrainer properties of probucol can be traced back to the fact that probucol captures free radicals continuing a radical chain-reaction ("chain propagating radicals") by giving off the hydrogen atoms of its hydroxyl groups. Probucol is in this way transformed into oxyl radicals which because of the resonance with the sulfur atoms in the para-position are electronically stabilized and because of the sterically-screening ortho-tert.-butyl substituents are unable to continue the radical chain [W. A. Pryor et al., J. Am. Chem. Soc. 110, 2224 (1988)].

In summary, at the moment the following partial picture for the pathogenesis of arteriosclerosis thus results:

Hypercholesterolemia is the result, inter alia, of a pathologically retarded LDL clearing owing to defective LDL receptor regulation and (or) structure. The prolonged half-life of the LDL particles in the plasma increases the probability of their oxidative modification. Oxidized LDL damage the endothelium owing to cytotoxic properties and are absorbed by macrophages via a special scavenger receptor without feedback control, the latter dying in the form of lipid-overloaded "foam cells", releasing endothelium-damaging lysosomal enzymes and initiating other pathogenic mechanisms [SMC proliferation (SMC=smooth muscle cell in the vascular wall) etc.] Foam cell formation and SMC proliferation count anatomically-pathologically as early processes of an arteriosclerosis which has not yet been demonstrated clinically.

Consequently, it appears extremely desirable to find active compounds which, after oral administration and good absorption, cause a marked lowering of the plasma cholesterol level via potent inhibition of HMG-CoA reductase and simultaneously have the probucol-typical antioxidative radical entrainer properties. However, this combination of properties is unknown among all hypolipidemic active compounds hitherto known [review: D. R. Illingworth, Drugs 33, 259 (1987)].

Only those HMG-CoA reductase inhibitors which fulfill the necessary condition that a suitably substituted aromatic compound is bonded via a heteroatom X to the 4 (R) -hydroxy-6(S) -methylene-3,4,5,6-tetrahydro-2H-pyran-2-one radical (formula A), which is essential for HMG-CoA reductase inhibition, or its ring-opened dihydroxycarboxylic acid form (formula B)

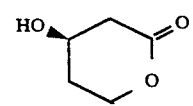

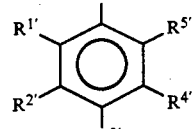

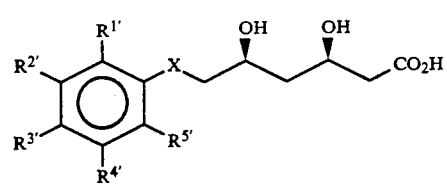

would have a chance of probucol-type properties. Compounds of the formulae A and B, in which X is oxygen or sulfur, have been described in a) European Patent Application A-0,216,127;
b) German Offenlegungsschrift 3,632,893 Derwent Abstract 88-99366/15);
c) German Offenlegungsschrift 3,819,999 (corresponding to EP-A-0,341,681, corresponding to U.S. patent application Ser. No. 350,428);
d) C. E. Stoker et al., J. Med. Chem. 28, 347 (1985) page 350.

According to German Offenlegungsschrift 3,819,999, particularly potent HMG-CoA reductase inhibitors are present if $R^{1'}$ in formula A or B has the meaning isopropyl or cyclopropyl and R⁵' has the meaning of a substituted phenyl, in particular p-fluorophenyl. Compounds of this type were more active in vitro and in vivo than mevinolin.

Although these ortho-substituents come close to the two tert.-butyl substituents of probucol with regard to their steric requirement, the compounds of the application c) possessed no probucol-analogous properties.

It has now surprisingly been found that on replacement of the p-substituent $R^{3'}$ by the group $Y-R^3$, where Y is a sulfur or oxygen atom and $R^3$ is a radical analogous to probucol

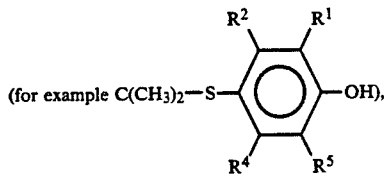

(for example $C(CH_3)_2-S-$⟨phenyl with $R^2, R^1, R^4, R^5$⟩$-OH$), compounds of the formula I are obtained which are provided with the antioxidative properties of probucol and also in some cases are very potent HMG-CoA reductase inhibitors.

It has been found that compounds of the formulae I and II

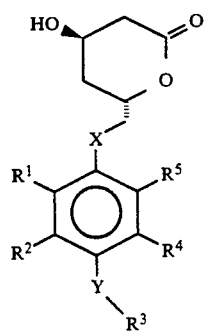

I

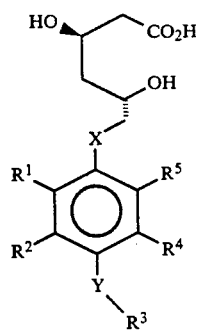

II and their pharmacologically tolerable salts with bases and their esters a) inhibit the enzyme HMG-CoA reductase more strongly than mevinolin and to about the same extent as compound C (3(R),5(S)-dihydroxy-6[-2-(4-fluorophenyl)-4,6-diisopropylphenoxy]hexanoic acid sodium salt, compare German Offenlegungsschrift 3,819,999, Example 8a), b) reduce cholesterol biosynthesis or the cholesterol content more strongly than mevinolin and compound C in cell culture, but in particular considerably more strongly than would be supposed solely on the basis of their inhibitory action on HMG-CoA reductase.

c) reduce the plasma cholesterol level more strongly than mevinolin in the same dose after p.o. administration to rabbits (5 mg/kg/day), but in particular reduce the plasma cholesterol level considerably more strongly than would be supposed solely on the basis of their inhibitory action on HMG-CoA reductase (cf. Table 4, and in this case also data for compound C).

d) cause a lowering of VLDL and a strong lowering of LDL after p.o. administration to Wistar rats (100 mg/kg/day), without HDL being lowered (in contrast to clofibrate and probucol). The lowering of plasma cholesterol in the rat test can unequivocally not be put down to HMG-CoA reductase inhibition, since HMG-CoA reductase inhibitors cause no plasma cholesterol lowering in the rat owing to rapid and strong counterregulation of the enzyme synthesis ("enzyme induction") [see, for example, Y. Tsujita et al., Biochim. Biophys. Acta 877, 50 (1986)].

e) inhibit the microsomal lipid peroxidation in vitro and are consequently radical inhibitors/antioxidants. In cases in which compounds of the formula I or II did not possess these properties (noticeably), they were discovered in the underlying phenol building blocks of the formula III

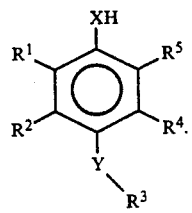

III

The latter were discovered as the more substantial metabolites on reaction of I or II with liver homogenate, i.e. they occur in vivo possibly as a metabolite of the compounds of the formula I or II.

The present invention therefore relates to compounds of the formula I

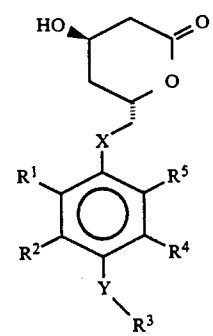

I in which

X and Y are identical or different and are an oxygen atom or a sulfur atom, $R^1$ and $R^5$ are both isopropyl or are different and are an isopropyl, cyclopropyl or phenyl radical, it being possible for the latter to be monosubstituted to trisubstituted in the nucleus by fluorine, chlorine, bromine, trifluoromethyl and/or alkyl or alkoxy each having 1 to 4 carbon atoms, $R^2$ and $R^4$ are identical or different and are hydrogen or an isopropyl, cyclopropyl or phenyl radical, it being possible for the latter to be monosubstituted to trisubstituted in the nucleus by fluorine, chlorine, bromine, trifluoromethyl and/or alkyl or alkoxy having 1 to 4 carbon atoms, $R^3$ is a) hydrogen, methyl or ethyl b) a straight-chain or branched alkyl radical having 3 to 8 carbon atoms, which can be substituted by the radical of the formula

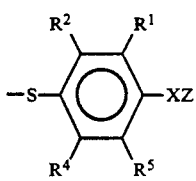

in which X, $R^1$, $R^2$, $R^4$ and $R^5$ have the abovementioned meanings and Z is either a hydrogen atom, a pharmacologically tolerable cation or the 4(R)-hydroxy-6-(S)-methylene-3,4,5,6-tetrahydro-2H-pyran-2-one radical of the formula

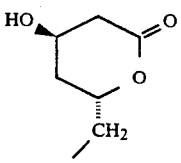

or the corresponding 3(R),5(S)-dihydroxyhexanoic acid-6-yl radical of the formula

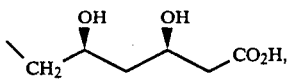

its pharmacologically tolerable salts with bases or its pharmacologically tolerable esters, c) cycloalkyl having 3 to 8 carbon atoms or a phenyl radical which can be monosubstituted to trisubstituted in the nucleus by halogen, trifluoromethyl and/or alkyl or alkoxy each having 1 to 4 carbon atoms, or d) acetyl with the condition that Y is oxygen, and the corresponding open-chain dihydroxycarboxylic acids of the formula II

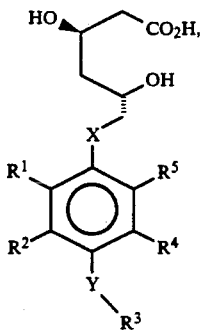

their pharmacologically tolerable salts with bases and their pharmacologically tolerable esters.

Preferred compounds are those in which the substituents $R^1$ and $R^5$ are not simultaneously phenyl and substituted phenyl or differently substituted phenyl.

The radicals in the formulae I and Ii preferably have the following meaning:

X: oxygen

Y: oxygen or sulfur $R^1$: isopropyl or cyclopropyl $R^2$: hydrogen, isopropyl or p-fluorophenyl $R^3$: hydrogen, acetyl, isopropyl, 9-fluorophenyl,

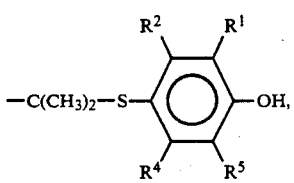

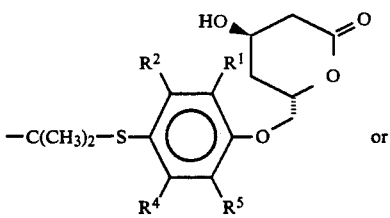

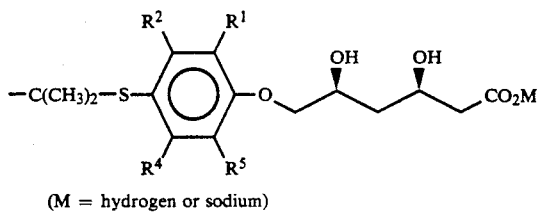

(M = hydrogen or sodium)

$R^4$: hydrogen, isopropyl or p-fluorophenyl $R^5$: isopropyl or p-fluorophenyl

The following compounds of the formula I are particularly preferred

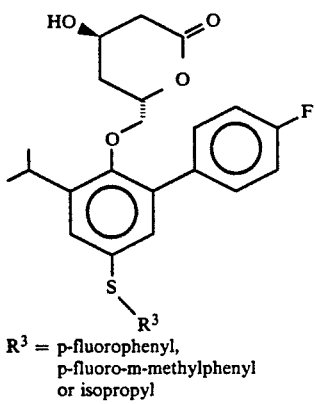

$R^3$ = p-fluorophenyl,
p-fluoro-m-methylphenyl
or isopropyl

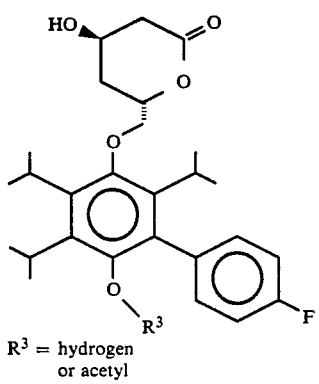

$R^3$ = hydrogen
or acetyl

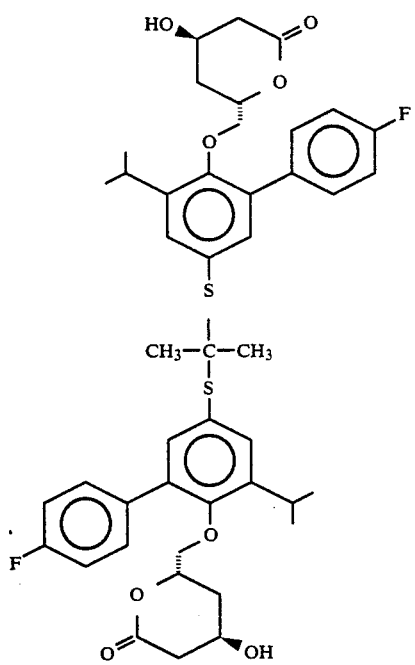

and the corresponding open-chain dihydroxycarboxylic acids of the formula II, their pharmacologically tolerable salts with bases and their pharmacologically tolerable esters.

The invention further relates to a process for the preparation of the compounds of the formula 1, and of the corresponding open-chain dihydroxycarboxylic acids of the formula II, their pharmacologically tolerable salts with bases and their pharmacologically tolerable esters.

The process comprises a) reacting appropriately substituted phenols or thiophenols of the formula III

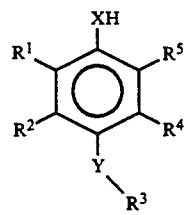

X, Y, $R^1$, $R^2$, $R^3$, $R^4$ and $R^5$ have the meanings indicated for formula I, with the optically pure mesylate of the formula IV

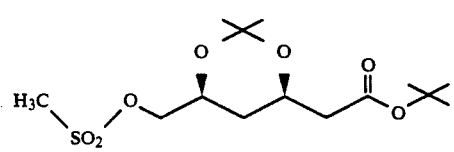

to give the acetonide of the formula V

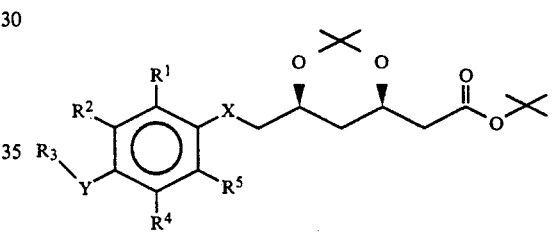

b) converting compounds of the formula V with removal of the protective group into tert.-butyl $\beta,\delta$-dihydroxycarboxylates of the formula II/I

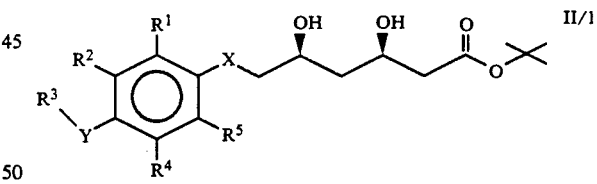

which X, Y, $R^1$, $R^2$, $R^3$, $R^4$ and $R^5$ have the meanings indicated for formula I, c) hydrolyzing the tert.-butyl esters of the formula II/1 to give salts of the formula II/2

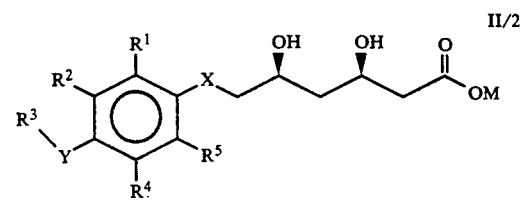

in which X, Y, $R^1$, $R^2$, $R^3$, $R^4$ and $R^5$ have the meanings indicated for formula I and M is the pharmacologically tolerable cation of a base, preferably the sodium cation, it also being possible to remove protective groups which may be present, d) cyclizing the tert.-butyl esters of the formula II/1 or, if appropriate, the salts of the formula II/2 to the β-hydroxylactones of the formula I

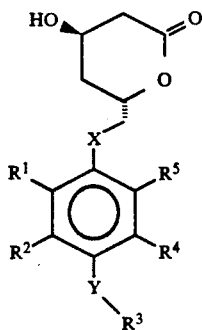

e) if appropriate converting the hydroxylactones of the formula I into the corresponding open-chain dihydroxycarboxylic acids of the formula II, their salts or their esters, if desired converting the salts or esters into the free dihydroxycarboxylic acids of the formula II or if desired converting the dihydroxycarboxylic acids II into the salts or esters.

As can be seen from the process described, the compounds of the formulae I and II and their salts and esters are prepared in optically pure form with the absolute configuration shown. In this absolute configuration, the compounds form a particularly preferred subject of the invention. Since malic acid, the starting material for the preparation of the mesylate of the formula IV, is also commercially available in the inverted absolute configuration [D(+)-malic acid] or as the racemate [DL-malic acid], the antipodes of the compounds of the formulae I and II and their salts and esters or the racemates of the compounds of the formulae I and II and their salts and esters can also be prepared in the same manner. Furthermore, more or less optically enriched compounds of both absolute configurations can be obtained from the racemates of the compounds of the formulae I and II and their salts and esters by the classical methods of racemate cleavage. The invention thus also relates to the antipodes of the compounds of the formulae I and II and their salts and esters, to the racemates, and to optically enriched compounds.

Process step a)

The mesylate of the formula IV is obtained by mesylation of the optically pure hydroxy compound of the formula VI

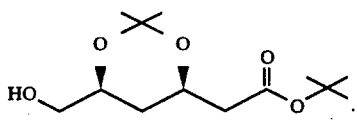

The preparation of the compound of the formula VI from commercially available L(−)-malic acid is described in EP-A-0,319,847. The reaction of the hydroxy compound VI to give the mesylate IV is carried out, for example, by reaction with methanesulfonyl chloride in the presence of a weak base. The methanesulfonyl chloride is advantageously employed in a small excess (1.05–1.5 equivalents). The use of a methylene chloride/pyridine mixture as the solvent is advantageous. Owing to the low thermal stability of many mesylates, it is recommended to carry out the reaction with cooling. The reaction temperature is advantageously kept near 0° C. by ice-cooling. With expedient working up (see Process Example 26), the mesylate IV crystallizes spontaneously and can be obtained in high yield and purity by filtering with suction and washing.

The coupling of III with IV is preferably carried out in the presence of a base in aprotic polar solvents. The use of potassium carbonate as a base and DMSO or HMPT as a solvent has proved particularly suitable. When using sulfur-containing compounds III (i.e. X and/or Y=S), HMPT is expediently used as the solvent. Occasionally, the use of a catalytic amount of 18-crown-6 accelerates the reaction and increases the yield of V. The mesylate IV is expediently employed in a small excess (about 1.1 equivalents). The coupling can be carried out in a temperature range from 40° to about 90° C. The purity of the crude product distinctly decreases with increasing reaction temperature. The optimum temperature and the associated duration of the reaction depend on the nature of the substituents, in particular the steric screening of the nucleophilic group XH, in the compound of the formula III. A reaction temperature of 60°–70° C. and a duration of reaction of about 12–18 hours was advantageous for the preparation of the particularly preferred compounds. Apart from the acetonide grouping, the two hydroxy groups of the mesylate IV can of course also be provided with other protective groups which are stable to the basic coupling conditions, for example tert.-butyldiphenylsilyl groups.

Process step b)

In principle, any of the numerous methods which have been described in the literature for the cleavage of ketals can be used for the preparation of the compounds of the formula II/1. The use of 2-normal aqueous hydrochloric acid as a catalyst in homogeneous organic solution (THF/ethanol) at room temperature is preferred.

Process step c)

This step is a basic ester hydrolysis step. It can be carried out using a large number of pharmacologically tolerable bases in aqueous, aqueous-organic or, if metal hydroxides are used as bases, alternatively in organic aprotic solvents. The use of a 1:1 (vol/vol) mixture of exactly 1.0 equivalent of an aqueous 1-normal sodium hydroxide solution and ethanol at room temperature is preferred. Excesses of sodium hydroxide solution should be avoided as sodium hydroxide and the sodium salt II/2 both have relatively good water solubility and can therefore only be separated with difficulty. The course of the hydrolysis can be monitored using silica gel TLC (chloroform/methanol 5:1). With most (but not with all) esters of the formula II/1, extensive hydrolysis under the conditions mentioned is also detected in that the initial suspension changes into a clear homogeneous solution.

Process step d)

The direct conversion of tert.-butyl esters of the formula II/1 into the hydroxylactones of the formula I is carried out using an excess of a number of strong acids, preferably organic acids. In principle, any organic solvent is suitable which has good dissolving power for the tert.-butyl ester II/1 and is sufficiently inert to the strong acid. The use of trifluoroacetic acid in methylene chloride solution at room temperature is preferred. The reaction time is as a rule 1–5 hours. TLC checking of the course of the reaction is recommended to avoid side reactions. It is advantageous to neutralize the reaction mixture by addition of sodium hydrogen carbonate with cooling and then to render it neutral with sodium carbonate. Excess sodium carbonate is to be avoided as the lactones I are very easily hydrolyzed to the salts II/2 even under weakly basic conditions. The lactones I can be obtained in high yield and purity by extraction.

The lactones I can be obtained from the salts II/2 by various procedures. In each case, the salts II/2 are converted into the free dihydroxycarboxylic acids of the formula II by careful acidification, followed by ethyl acetate extraction. The latter can be cyclized to the lactone I by treatment with 1-1.5 equivalents of a dehydrating reagent, for example N,N'-dicyclohexylcarbodiimide or, preferably, a water-soluble carbodiimide such as N-cyclohexyl-N'-[2'-(N''-methylmorpholinium-)ethyl]carbodiimide para-toluenesulfonate (Cf. M. Fieser "Reagents for Organic Synthesis" 1, 181 and 11, 151) in an inert organic solvent, preferably methylene chloride, at 10°-35° C., preferably at room temperature. Better yields and product purities are as a rule obtained if, instead, the carboxyl group of the free dihydroxycarboxylic acids of the formula II is reacted to give an intermediate derivative which is activated with regard to an intramolecular nucleophilic attack of the δ-hydroxy group. The literature describes a large number of methods of this type for carboxyl activation. The formation of acid halides, acid imidazolides, active esters or mixed anhydrides is very widespread. The carboxylic acid of the formula II is preferably reacted with 1.1 equivalents of triethylamine and 1.0 equivalent of ethyl chloroformate at 0°-10° C. in absolute THF. The lactones of the formula I are formed in nearly quantitative yield in reaction times of 1-2 hours.

Process step e)

These transformations are trivial and are to be carried out corresponding to the instructions in the prior art, for example with bases in the case of salt formation.

Substituted phenols or thiophenols of the formula III are required as starting materials for carrying out process step a). Compounds of the formula III in which X, Y, $R^1$, $R^2$, $R^3$, $R^4$ and $R^5$ have the meanings indicated for formula I are new. They are therefore also included in the subject of the present invention.

In German Offenlegungsschrift 3,819,999, a process for the arylation of phenols is proposed which consists in first subjecting the phenols to an electrophilic aromatic halogenation (halogen=bromine or iodine) and then treating the monohalophenol under palladium(O) catalysis with an aryl Grignard compound, a position-specific halogen-aryl replacement taking place: the aryl radical only occurs in the position in which the halogen atom was previously found. The compounds of the formula III were synthesized using this reaction as a key step. The thiophenols can be prepared from the phenols in accordance with the instructions in DE-A 3,632,893.

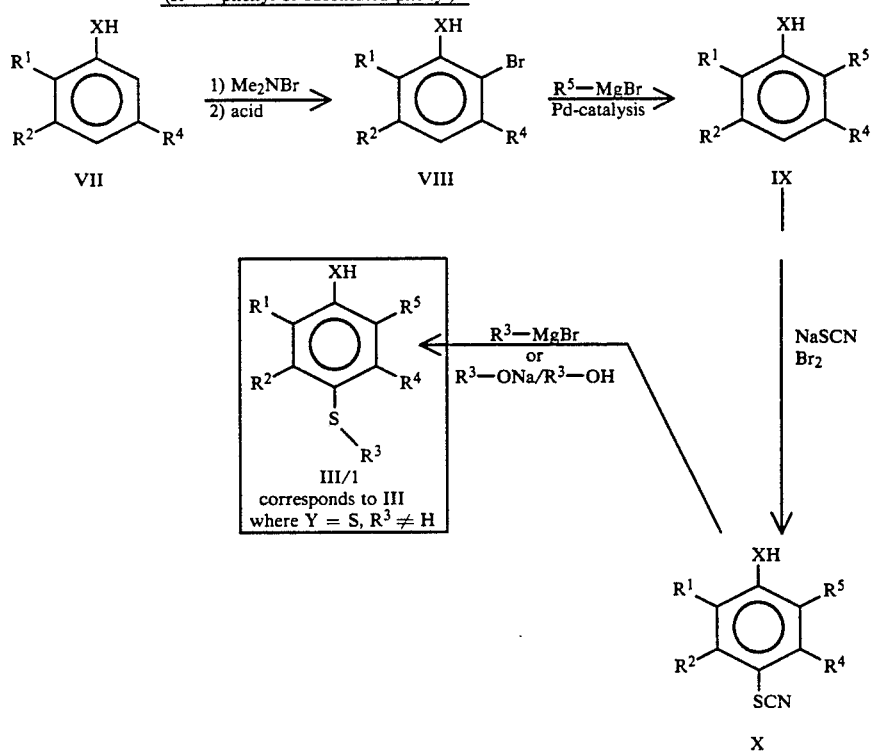

-continued
Scheme 1
($R^5$ = phenyl or substituted phenyl)

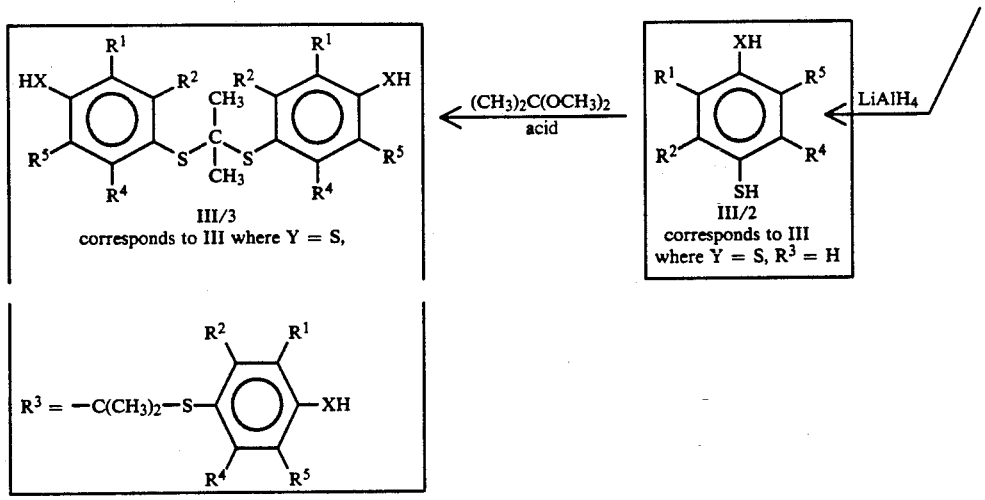

III/3
corresponds to III where Y = S,

III/2
corresponds to III
where Y = S, $R^3$ = H $R^3 = -C(CH_3)_2-S-$ (ring with $R^2$, $R^1$, $R^4$, $R^5$, XH)

Starting materials for the synthesis of compounds of the formula III according to scheme 1 are phenols or thiophenols of the formula VII or, according to scheme 3, benzenes of the formula XIII. The compounds VII are commercially available or known from the literature, if $R^2$ or $R^4$ do not have the meaning of a (substituted) phenyl radical. If $R^2$ or $R^4$ in formula III is intended to have the meaning of a (substituted) phenyl radical, the compounds VII can be obtained analogously to the reaction described above, or the synthesis according to scheme 3 can be used.

A regiospecific ortho-halogenation of phenols can be achieved using N-haloamines in accordance with the instructions in the literature [E. Schmitz, I. Pagenkopf, J. Prakt. Chem. 327, 998 (1985)]. Ranges of application and process variants were described in detail by Schmitz and Pagenkopf. Preferably, 1.1 equivalents of a commercially available 40% strength aqueous dimethylamine solution are reacted at about −10° C. with the aqueous sodium hypobromide solution formed from 3.2 equivalents of sodium hydroxide and 1.02 equivalents of bromine to give N-bromodimethylamine, which is extracted using carbon tetrachloride, then dried. This solution is then added dropwise at −10° C. to a solution of 1 equivalent of the compound VII in carbon tetrachloride. The ortho-brominated dimethylammonium salt precipitates, and is filtered off with suction and converted into the free compound VIII by boiling with 2N sulfuric acid. Since, according to scheme 1, phenyl or substituted phenyl is introduced as the radical $R^5$, compound VIII is reacted with the phenyl Grignard reagent $R^5$-MgBr under palladium catalysis to give compounds of the formula IX. The variants for carrying out the coupling reaction and alternatives for palladium have been proposed in German Patent Application 38 19 999.8. For the conversion of VIII and IX, preferably 3 equivalents of the Grignard reagent formed from $R^5$-Br and a small excess of magnesium turnings are prepared in THF and this solution is then transferred at 60° C. to a solution of 1 equivalent of the compound VIII and 3-5 mol-% of tetrakis(triphenylphosphine)palladium(O) in THF. Complete reaction takes place, depending on the nature of the substituents $R^1$, $R^2$, $R^4$ and $R^5$, in the course of 1 hour–12 hours at 60° C. The introduction of the sulfur function into the para-position, compounds X being formed, is carried out by thiocyanation. There are several procedures for this step, which have been described in detail and compared (for example J. L. Wood in Org. React. J, 240-266 (1946) and J. H. Clark et al., J. Chem. Soc. Chem. Commun., 81 (1989)]. Preferably, 1 equivalent of the compound of the formula IX and 5 equivalents of sodium thiocyanate are suspended in methanol and a solution of 1.5 equivalents of bromine in methanol is slowly added dropwise at about 15° C. The reaction is based on the formation and in situ reaction of dithiocyanogen $(SCN)_2$.

If a solution of a thiocyanate of the formula X is added dropwise, preferably at 25°-50° C., to preferably 6 equivalents of an alkyl or aryl Grignard compound $R^3$-MgBr, preferably in THF as solvent, thioethers of the formula III/I are obtained. If $R^3$ is an aliphatic radical, the thioether III/1 is also obtained if a solution of the thiocyanate of the formula X and an excess of the sodium alkoxide $R^3$ONa (preferably about 2 equivalents) is heated under reflux in the alcohol $R^3$OH. The thioethers of the formula III/I correspond to the formula III, with the limitation that Y must be sulfur. Numerous methods are known to convert thiocyanates into the corresponding thiols. A review is to be found, f or example, in K.-D. Gundermann and K. Hümke in "Methoden der Organischen ChemieII" [Methods of Organic Chemistry] (Houben-Weyl), volume E 11; "Organische Schwefelverbindungen, Teil 1" [Organic Sulfur Compounds, Part 1], Thieme Verlag (Stuttgart, 1985) page 59: "Thiole aus Thiocyansäureestern" [Thiols from Thiocyanic Acid Esters]. Preferably, the reductive cleavage of the thiocyanates of the formula X to give thiols of the formula III/2 is carried out using about 1.7 mole equivalents of lithium aluminum hydride in tetrahydrofuran under reflux. The yields in this procedure are very high (>90%). In the presence of atmospheric oxygen, the thiols of the formula III/2 undergo rapid oxidative dimerization to the corresponding disulfides. They are therefore expediently prepared by thorough degassing of the reaction solution under an inert gas atmosphere. The thiols of the formula III/2 correspond to the formula III, with the limitation that Y is sulfur and $R^3$ is hydrogen.

There are several alternative methods for the introduction of the thiol grouping into aromatic compounds of the formula IX. A review is to be found, for example, in K.-D. Gundermann and J. Hümke in "Methoden der Organischen Chemie" [Methods of Organic Chemistry] (Houben-Weyl), volume E 11; "Organische Schwefelverbindungen, Teil 1" [Organic Sulfur Compounds, Part 1], Thieme Verlag (Stuttgart 1985), pages 32-63: "Herstellung von Thiolen" [Preparation of Thiols]. A synthetic route is described in detail in scheme 1.

The reaction of the thiols of the formula III/2 to give the acetone dithioketals of the formula III/3 is possible in principle using acetone in the presence of an acidic catalyst analogously to the method described for probucol. [M. B. Neuworth et al., J. Med. Chem. 13, 722 (1970)].

Compounds of the formula III/3 are obtained in 85-100% yield when the thiols of the formula III/2 are heated to about 80° C. in the presence of catalytic amounts of p-toluenesulfonic acid in an inert solvent, preferably benzene, containing 1.25-1.50 equivalents of 2,2-dimethoxypropane. The reaction time depends on the nature of the substituents $R^1$, $R^2$, $R^4$ and $R^5$ and is as a rule 2-12 hours. The polar, mixed oxygen/sulfur ketal of the formula XI

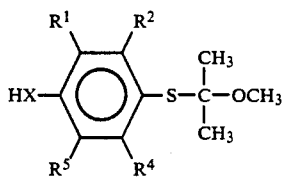

XI occurs as an intermediate of the reaction and is the principal product when the reaction is carried out at room temperature (1-2 hours). It is slowly converted in the reaction mixture at room temperature, and rapidly at about 80° C., into the less polar product of the formula III/3. The thioketals of the formula III/3 correspond to the formula III, with the limitation that Y is sulfur and $R^3$ is the radical

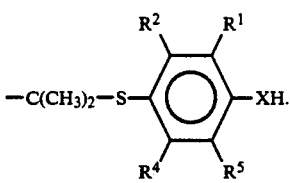

The process according to the invention is illustrated below by the reaction of compound III/3 to give the final products of the formula I according to scheme 2.

The reaction of the thioketals of the formula III/3 with the mesylate IV according to process step a) leads to two different coupling products, namely the monocoupling product V/1 and the dicoupling product XII. V/1 and XII can be separated by column chromatography without problems. They are always both formed in the coupling, but their ratio can be influenced by means of the reaction conditions. If, for example, only 1.2 moles of the mesylate IV is used per mole of thioketal III/3, V/1 and XII are formed approximately in the ratio 2:1 (about 70% total yield). On the other hand, if 2.5 moles of the mesylate IV are employed per mole of thioketal XII/3 and the reaction time is lengthened, the ratio V/1 to XII is <1:3.

The separated products V/1 and XII can then be converted into the mono(hydroxylactones) of the formula I/1, the bis-(hydroxylactones) of the formula I/2 (both formulae are special cases of the formula 1), their open-chain dihydroxycarboxylic acids of the formula II, their salts or their esters according to process steps b), c), d) and, if desired, e).

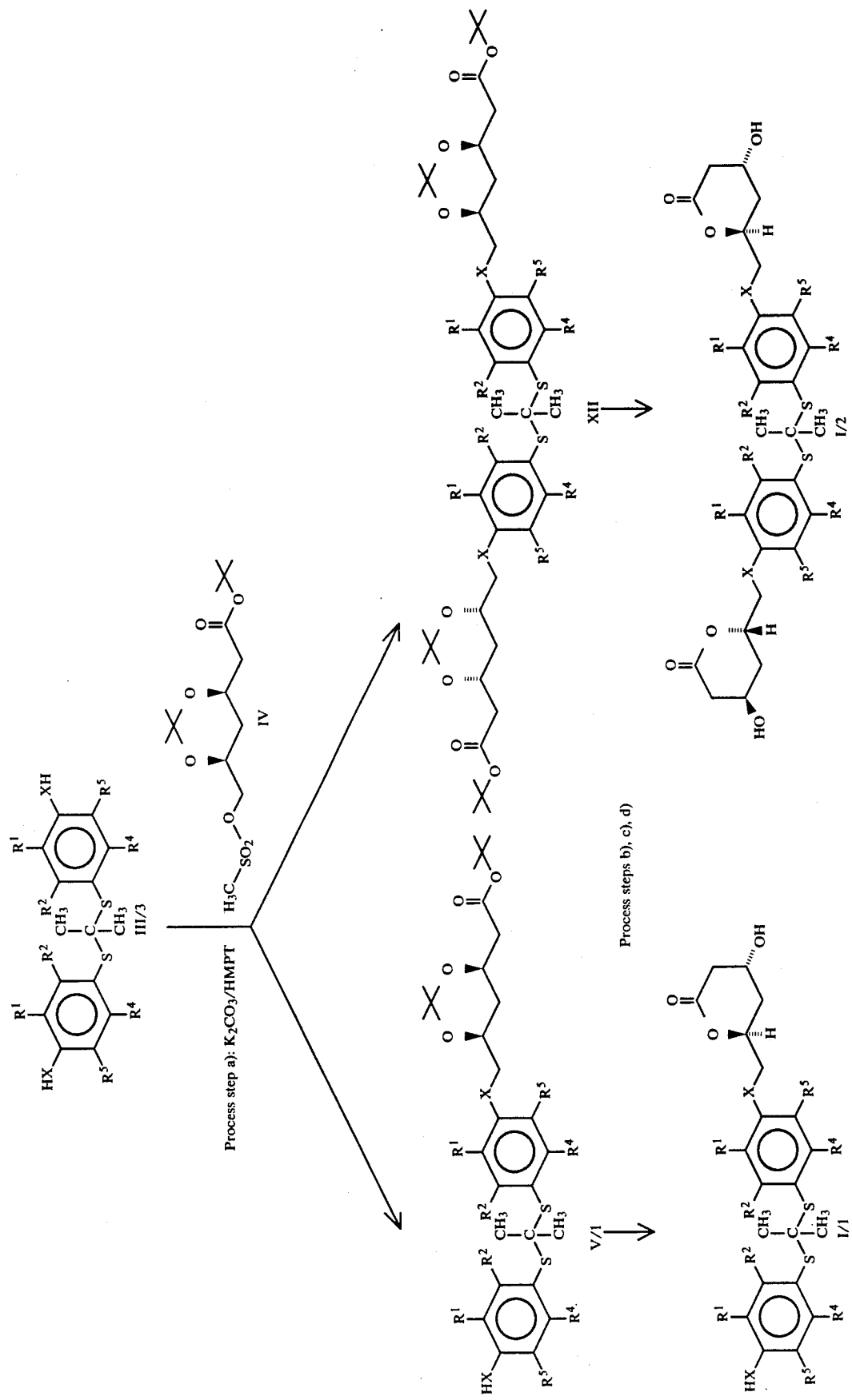

-continued
Scheme 2
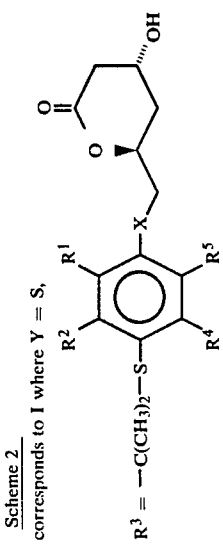
corresponds to I where Y = S,
R³ = —C(CH₃)₂—S—
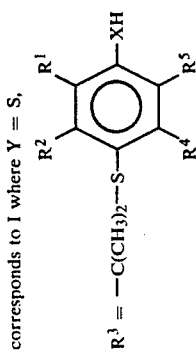
corresponds to I where Y = S,
R³ = —C(CH₃)₂—S—

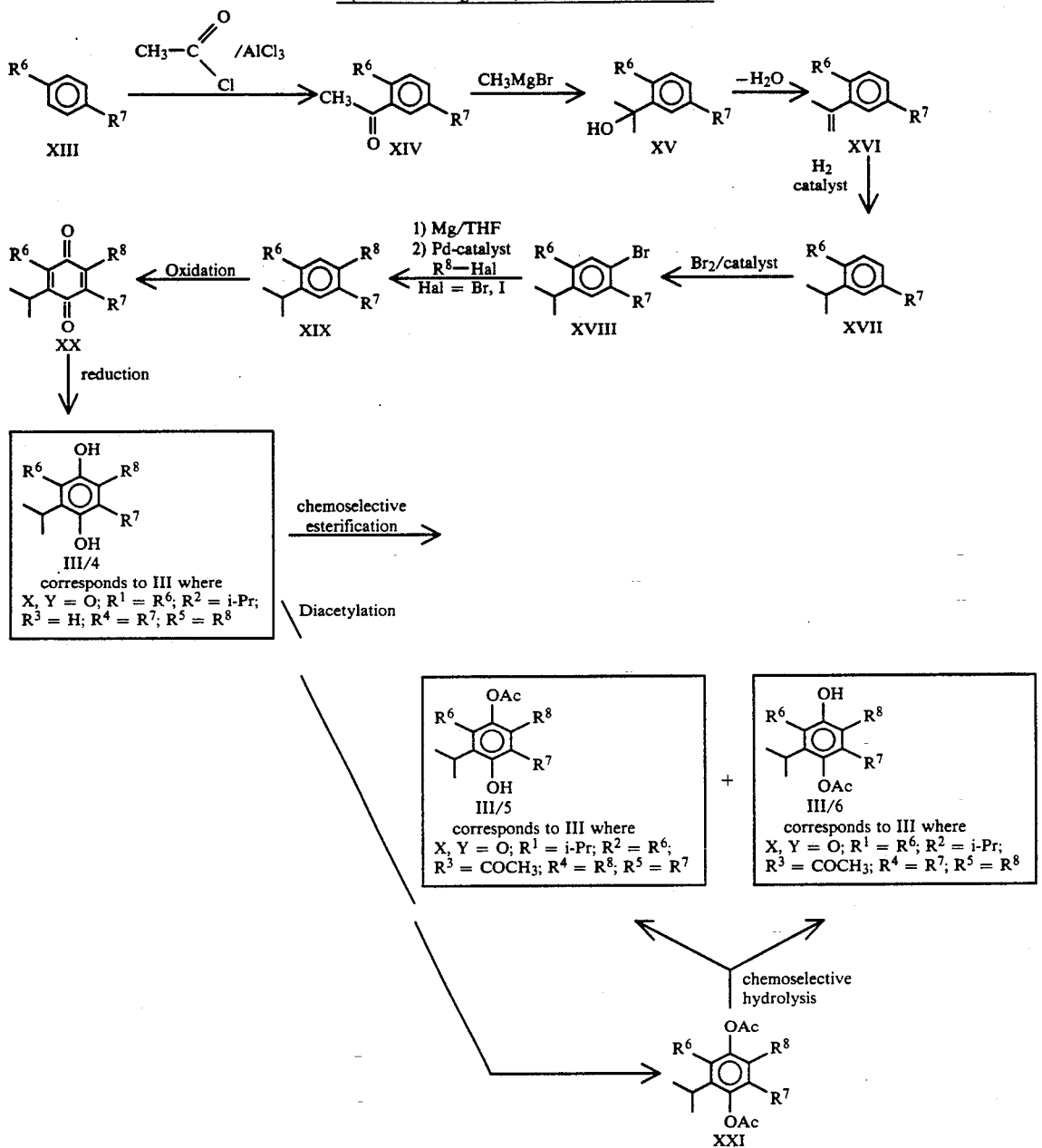

Scheme 3
(for the meaning of $R^6$, $R^7$, $R^8$ and $R^9$ see text)

Substituted hydroquinones (phenols of the formula III in which X and Y are oxygen) of the formulae III/4, III/5 and III/6, which are all special cases of the building blocks with the formula III, can be prepared according to the synthesis sequence indicated in scheme 3. The unusual feature of this process is that the two hydroxy groups are only introduced into the aromatic hydrocarbon of the formula XIX at the end of the sequence. Furthermore, the two hydroxy groups of the compounds of the formula III/4 can be differentiated by complementary processes in such a way that either one or the other hydroxy group can specifically undergo coupling with the mesylate IV. In monoacetates of the formula III/5, for example, the "upper" hydroxy group of the hydroquinones III/4 was protected; only the "lower" hydroxy group remains capable of coupling for the reaction with compounds of the formula IV and thus obtains the meaning of the XH group of the formula III where X=oxygen. The isopropyl group and the substituent $R^7$ the formula III/5 thus correspond to the substituents $R^1$ and $R^5$ of the formulae I to III, while the substituents $R^6$ and $R^8$ of III/5 correspond to $R^2$ and $R^4$ of I to III.

In the monoacetate of the formula III/6, on the other hand, the "lower" hydroxy group of the hydroquinones III/4 is protected. In III/6 the "upper" hydroxy group consequently has the meaning of the XH group of the formula III where X=oxygen. The isopropyl group and the substituent $R^7$ of the formula III/6 thus correspond to the substituents $R^2$ and $R^4$ of the formulae I to III, while the substituents $R^6$ and $R^8$ of III/6 correspond to $R^1$ and $R^5$ of I to III.

It is known that, depending on the choice of the complementary monoacetylation process, the substituent pairs $R^6/R^8$ and i-Pr/$R^7$ can confer the meaning of ortho-substituents $R^1/R^5$ or metasubstituents $R^2/R^4$ in the final products of the formulae I and II. The direct chemoselective esterification is always complementary in compounds of the formula III/4 to the two-step process for diacetylation, followed by chemoselective hydrolysis. The substituent pair i-Pr/$R^7$ has either a higher or a lower steric requirement than the substituent pair $R^6/R^8$.

Under mild conditions, the monoacetylation takes place distinctly more rapidly on the less sterically hindered of-the two hydroxy groups of III/4. On the other hand, if a diacetylation to give XXI is forced as a result of more drastic reaction conditions and an excess of the acetylating agent, the sterically less hindered hydroxy group is liberated distinctly more rapidly than the hindered one in the subsequent hydrolysis. The opposite product is preferably thus obtained compared to the direct monoacetylation.

Starting materials for the synthesis of the hydroquinones III/4 or the complementary protected hydroquinones of the formulae III/5 and III/6 are the substituted benzenes of the formula XIII, which are known from the literature and, for the most part, commercially available. Depending on which of the two complementary acetylations is later carried out, $R^6$ has the meaning which has been indicated for $R^1$ or $R^5$ in the formula I and $R^7$ has the meaning which has been indicated for $R^2$ or $R^4$ in the formula I—or vice versa.

Compounds of the formula XIV are obtained by Friedel-Crafts acetylation of the benzenes XIII. The reaction is carried out using a small molar excess, preferably about 1.05 equivalents, of acetyl chloride in the presence of an excess of a Lewis acid, preferably about 1.2 equivalents of aluminum chloride, in an inert dry solvent, preferably carbon disulfide. Optimum reaction temperatures and times depend on the nature of the substituents $R^6$ and $R^7$. As a rule, a temperature of close to $-10°$ C. and a time of 1–about 6 hours is preferred. The acetylation takes place almost exclusively in the ortho-position to the substituents $R^6$ or $R^7$. If $R^6$ and $R^7$ are identical, only one product is formed. If $R^6$ and $R^7$ are different, two products are formed, which have to be separated. As a rule, purification or separation of the methyl ketones XIV can be carried out by high vacuum distillation.

The alcohols of the formula XV are obtained in virtually quantitative yield if an excess, preferably about 1.4 equivalents, of a commercial ethereal methylmagnesium halide solution (for example a commercially available ethereal methylmagnesium iodide solution) is added dropwise to an ethereal solution of the methyl ketone XIV so that reflux is maintained. In principle, these reactions can be worked up by extraction and the alcohols XV purified by crystallization. However, it is advantageous to eliminate water directly from the crude alcohols XV by heating them under reflux in a water separator in the presence of a catalytic amount of a strong acid, preferably para-toluenesulfonic acid, in a solvent which forms a low-boiling azeotrope with water, but is only sparingly miscible with this, preferably benzene or toluene.

The crude olefins of the formula XVI are converted into the compound of the formula XVII by catalytic hydrogenation. A large number of catalysts are described in the literature which are suitable for reactions of this type. For reasons of safety and easier feasibility, the hydrogenation is preferably carried out at room temperature under 1 atm of hydrogen. The use of 1–2% by weight of 10% palladium on carbon and of n-hexane as solvent has proven suitable for this purpose. As a rule, the compounds of the formula XVII can be purified by vacuum distillation, but other physical separation processes, such as recrystallization or chromatography, are of course also possible.

Owing to a combination of electronic and steric factors, the electrophilic aromatic bromination takes place under mild conditions with high regioselectivity with the formation of compounds of the formula XVIII. In order to avoid multiple bromination, an excess of bromine should be avoided. Carbon tetrachloride has proven suitable as an inert solvent and a spatula tip full of iron powder as a catalyst. The reaction is preferably carried out at or below $-10°$ C. in order to achieve high selectivity.

The replacement of the bromine atom of XVIII by a (substituted) aryl radical $R^6$ is best carried out by reacting XVIII with an equivalent of magnesium turnings in THF under reflux to give the corresponding Grignard compound. This Grignard solution is then transferred under inert gas pressure in THF to a solution of about 1.05 equivalents of a (substituted) aryl bromide or aryl iodide $R^8$-Hal and about 0.01 equivalent of a palladium(O) catalyst, preferably tetrakis(triphenylphosphine)palladium(O), and the reaction mixture is heated under reflux. Frequently, the reaction can also be carried out by preparing the Grignard compound $R^8$-MgHal and then adding this to a solution of the aryl bromide XVIII and a catalytic amount of Pd(PPh$_3$)$_4$ in THF. Variants for carrying out the coupling reaction and alternatives for palladium have been proposed (cf. German Offenlegungsschrift 3,819,999). As a rule, the products of the formula XIX can be purified by distillation in a pump vacuum.

The reaction of the hydrocarbons of the formula XIX to give the quinones of the formula XX can be achieved using a number of oxidants. As a rule, the yield of the reaction distinctly increases with increasing substitution of the starting compound.

The addition of a large excess of a 5:1 (vol/vol) mixture of trifluoroacetic acid and 70% strength aqueous hydrogen peroxide at about $-20°$ C. to the hydrocarbon XIX is preferred. No heat of reaction or reaction is observed at this temperature. If the cooling bath is then removed and the mixture is stirred while warming to room temperature, a sudden, extremely exothermic initiation of the reaction is observed in the temperature range from about $+10°$ C. to $+20°$ C. Intensive cooling of the reaction flask and the reflux condenser is then necessary in order to keep the reaction under control. The pure, intensively yellow quinones XX are obtained from the crude reaction product by column chromatography or more simply by recrystallization. The quinones of the formula XX can be reduced to the hydroquinones of the formula III/4 using various reagents. H. Ulrich and R. Richter give a review in "Methoden der Organischen Chemie" [Methods of Organic Chemistry] (Houben-Weyl), volume VII/3a "Chinone Teil 1" [Quinones Part 1], Georg Thieme Verlag, Stuttgart (1977), pages 648–653: "Umwandlung von p-Chinonen durch Reduktion" [Transformation of p-quinones by reduction]. It is advantageous to add about 5 mole equivalents of sodium borohydride to a solution of the quinones XX in ethanol under inert gas. The course of the reaction is detected by the decolorization of the originally yellow solution. The ethanol is then removed in vacuo and the residue is decomposed with intensive cooling using degassed hydrochloric acid. The aqueous phase is immediately extracted using degassed diethyl ether and the ether is removed in vacuo. The hydroquinones of the formula III/4 remain as colorless powders which are washed with, for example, n-pentane and filtered off with suction under inert gas. These hydroquinones undergo very easy oxidation, especially in solution, being reconverted into the yellow quinones XX. All solvents should therefore be oxygen-free in the preparation of III/4. The hydroquinones III/4 are best reacted directly, also under oxygen-free conditions, to give the monoacetates III/5 or III/6, which are hardly sensitive to oxidation.

For the regioselective preparation of the monoacetates of the formulae III/5 and (or) III/6, the hydroquinones of the formula III/4 are reacted, for example at 0° C., with 1.1–1.5 equivalents of acetic anhydride in the presence of a base, preferably in anhydrous pyridine as a solvent. The reaction time is 1–3 days depending on the nature of the substituents $R^6$, $R^7$ and $R^8$. In addition to a little starting material III/4 and diacetate XX, the two monoacetates III/5 and III/6 are obtained with a selectivity which is 4:1 to about 20:1, depending on the nature of the substituents $R^6$, $R^7$ and $R^8$.

The two monoacetates can be separated from one anothers, and from the quinone XX and the diacetate XXI#by column chromatography on silica gel. In the eluent cyclohexane/ethyl acetate 9:1. the sterically more greatly hindered (formed to a smaller extent) monoacetate has a somewhat larger $R_f$ value than the sterically less hindered (formed to a greater extent) monoacetate (principal product). The diacetate XXI is distinctly more polar. Mono- and diacetates of the formulae III/5, III/6 and XXI are solids which, if required, can be further purified by recrystallization.

For the specific preparation of the diacetates of the formula XXI, the hydroquinones of the formula III/4 are reacted with an excess, preferably 3–4 equivalents of acetic anhydride, in the presence of a base, preferably in anhydrous pyridine as the solvent. The reaction temperature is about 0°–40° C. depending on the nature of the substituents $R^6$, $R^7$ and $R^8$ and the reaction time is about 1 hour to several days.

Both in the mono- and the diacetylation, other acylating agents, for example acetyl chloride, mixed anhydrides of acetic acid, acetic acid imidazolide etc. can also be employed instead of acetic anhydride.

Occasionally, the yields in the mono- or diacetylation are distinctly increased if 4-dimethylaminopyridine (DMAP, preferably 5–10 mol-%) is employed as a catalyst, triethylamine is employed as a base and acetic anhydride is employed as an acylating agent [G. Höfle, W. Steglich, H. Vorbrüggen, Angew. Chem. Int. Ed. 17, 569 (1978)]. All mild methods of ester cleavage are in principle utilizable for the chemoselective (regioselective) hydrolysis of the diacetates of the formula XXI. These methods are prior art. It is crucial that only a little more than 1 equivalent of the base is employed (in order largely to avoid the hydrolysis of both acetyl groups) and that the reaction temperature is kept so low that the hydrolysis requires several days (maximum selectivity).

The use of 1.1 equivalents of lithium hydroxide in 1,2-dimethoxyethane/water 3:1 (vol/vol) is expedient. Optimum reaction temperatures and times depend on the nature of the substituents $R^6$, $R^7$ and $R^8$. As a rule, hydrolysis at room temperature, which usually requires 1–5 days, leads to selectivities of 2–5 to 1.

High cholesterol levels, and the oxidative modification of the LDL and the formation of "foam cells" with consequent pathogenic processes resulting from this has been associated with a number of disorders which are considered as consequences of arteriosclerosis, for example coronary heart disease and cardiac infarct. The lowering of raised cholesterol levels and the avoidance of LDL oxidation is therefore a therapeutic aim for the prevention and treatment of such disorders. A starting point is the inhibition or reduction of endogenous cholesterol synthesis. Inhibitors of HKG-CoA reductase block cholesterol biosynthesis at an early stage. They are therefore suitable for the prevention and treatment of disorders which are caused by an increased cholesterol level. A reduction or lowering of the endogenous synthesis leads to an increased absorption of cholesterol from the plasma into the cells. An additional effect can be achieved by simultaneous administration of bile acid-binding substances such as anion exchangers. The increased bile acid excretion leads to increased resynthesis and thus to increased cholesterol degradation (M. S. Brown, P. T. Kovanen and J. L. Goldstein, Science 212, 628 (1981); M. S. Brown and J. L. Goldstein, Spektrum der Wissenschaft 1985, 96). The compounds according to the invention are inhibitors of HMG-CoA reductase. They are therefore suitable for the inhibition or reduction of cholesterol biosynthesis and thus for the prevention or treatment of disorders which are caused by raised cholesterol levels in the blood, in particular coronary heart disease, atherosclerosis and similar disorders. There are indications (cf. Tab. 1–4) that the compounds according to the invention moreover have a plasma cholesterol-lowering action according to another kind of mechanism, which increases the plasma cholesterol reduction achieved by the mechanism of HKG-CoA reductase inhibition. The compounds according to the invention and (or) their building blocks of the formula III moreover have an antioxidative, radical-inhibitory action. The building blocks of the formula III are moreover metabolites of the compounds according to the invention.

The invention therefore also relates to pharmaceutical preparations based on compounds of the formula I or the corresponding dihydroxycarboxylic acids of the formula II, their salts and esters, and the use of these compounds as pharmaceuticals, in particular for the treatment of hypercholesterolemia.

The compounds of the formula I or II and the corresponding salts or esters are administered in various dosage forms, preferably orally in the form of tablets, capsules or liquids. Depending on the body weight and constitution of the patient, the daily dose varies in the range from 1 mg to 2,500 mg, but preferably in the dose range 10 to 100 mg.

The compounds according to the invention can be used as lactones of the formula I, in the form of the free acids of the formula II or in the form of pharmaceutically acceptable salts or esters, in particular dissolved or suspended in pharmacologically acceptable organic solvents such as mono- or polyhydric alcohols such as, for example, ethanol or glycerol, in triacetin, oils such as, for example, sunflower oil or cod liver oil, ethers such as, for example, diethylene glycol dimethyl ether or, alternatively, polyethers such as, for example, polyethylene glycol or, alternatively, in the presence of other pharmacologically acceptable polymer excipients such as, for example, polyvinylpyrrolidone or other pharmaceutically acceptable additives such as starch, cyclodextrin or polysaccharides. In addition, the compounds according to the invention can be combined with additives which bind bile acids, in particular nontoxic, basic anion exchanger resins which bind bile acids in a form which cannot be absorbed in the gastrointestinal tract. The salts of the dihydroxycarboxylic acids can also be administered as an aqueous solution.

The inhibition of cholesterol biosynthesis or the plasma cholesterol reduction by the compounds of the formulae I and II according to the invention were determined in various in vitro and in vivo test systems.

1) Inhibition of HKG-CoA reductase activity in solubilized enzyme preparations from rat liver microsomes HMG-CoA reductase activity was measured on solubilized enzyme preparations from liver microsomes of rats which had been induced by conversion into the day/night rhythm using cholestyramine (®Cuemid). (S,R)$^{14}$C-HMG-CoA was used as a substrate, and the concentration of NADPH was maintained during the incubation by a regenerating system. The separation of $^{14}$C-mevalonate from substrate and other products (for example $^{14}$C-HMG) was carried out by column elution, the elution profile of each individual sample being determined. The regular addition of $^3$H-mevalonate was avoided as the determination gives the data relative to the inhibitory action. The enzyme-free control, the enzyme-containing normal mixture (=100%) and those containing preparation additives were in each case treated together in one series of experiments. The sodium salts of the dihydroxycarboxylic acids of the formula II were always employed as the preparation in this test. Each individual value was formed as the mean value of 3 parallel samples. The significance of the mean value differences between preparation-free and preparation-containing samples was evaluated by the t-test. The following inhibitory values, for example, were determined for the HMG-CoA reductase from the sodium salts of the compounds of the formula II according to the invention by the method described above (IC$_{50}$ (mol/l); molar concentration of the compound per liter which is necessary for a 50% inhibition).

TABLE 1

| | IC$_{50}$ (mol/l) |
|---|---|
| Standard mevinolin sodium salt | $8 \times 10^{-9}$ |
| Compound C (German Offenlegungsschrift 3,819,999, Example 8a) | $2.3 \times 10^{-9}$ |
| Example | |
| 1 | $6 \times 10^{-9}$ |
| 2 | $2 \times 10^{-9}$ |
| 3 | $4 \times 10^{-9}$ |
| 4 | $8 \times 10^{-9}$ |
| 5 | $8 \times 10^{-9}$ |
| 6 | $3 \times 10^{-9}$ |
| 7 | $1 \times 10^{-9}$ |
| 8 | $2 \times 10^{-9}$ |
| 9 | $4 \times 10^{-9}$ |

2) Inhibition of cholesterol biosynthesis in cell cultures (EEP G2 cells)

Determination of the inhibition of the incorporation of $^{14}$C-sodium acetate in cholesterol Monolayers of HEP G2 cells in lipoprotein-free medium were preincubated with various concentrations of the sodium salts of the dihydroxycarboxylic acids of the formula II for 1 hour. After adding $^{14}$C-labeled sodium acetate, the incubation was continued for 3 hours. Tritium-labeled cholesterol was added as an internal standard and an aliquot of the cells was subjected to alkaline hydrolysis. The lipids were extracted using chloroform/methanol 2: 1. After adding carrier cholesterol, the lipid mixture was preparatively separated on TLC plates using chloroform/acetone 9: 1. The cholesterol zone was made visible by staining with iodine vapor, additionally detected using a TLC radio scanner and then scraped off. The amount of $^{14}$C-cholesterol formed was determined scintigraphically and related to mg of cell protein. The same procedure was carried out with cells from the Bame culture without preincubation with a test compound (so-called "solvent control"). The potency of the test compounds was determined by comparison of the biosynthesized $^{14}$C-cholesterol in test runs and in "solvent control". The external standard was mevinolin sodium salt. The IC$_{50}$ and IC$_{70}$ values (IC$_{50}$ or IC$_{70}$ is the molar (mol/liter) concentration of the compound which is necessary for a 50 or 70% inhibition) varied somewhat for different test batches. The mean values for mevinolin sodium salt were IC$_{50}=5\times10^{-8}$M and IC$_{70}=1.5\times10^{-7}$M. The measured ICs for test compounds (sodium salts of the dihydroxycarboxylic acids of the formula II) (Table 2) were corrected by the deviation of mevinolin sodium from its mean value. Mevinolin sodium was assigned a relative potency of 100.

TABLE 2

| | IC$_{50}$ (M) | IC$_{70}$ (M) | Relative potency in % |
|---|---|---|---|
| Standard mevinolin sodium salt | $5.0 \times 10^{-8}$ | $1.5 \times 10^{-7}$ | 100 |
| Compound C | $2.7 \times 10^{-8}$ | $7 \times 10^{-8}$ | 185 (214) |
| Example | | | |
| 1 | $4.3 \times 10^{-9}$ | $\sim 8 \times 10^{-10}$ | 1163 (18750) |
| 2 | $2.2 \times 10^{-9}$ | | 2273 |
| 3 | $3.8 \times 10^{-9}$ | | 1316 |
| 4 | $8.0 \times 10^{-9}$ | | 625 |
| 5 | $9.2 \times 10^{-9}$ | | 543 |
| 6 | $1.7 \times 10^{-6}$ | | 3 |
| 7 | $9.2 \times 10^{-7}$ | | 5 |
| 8 | $4.0 \times 10^{-9}$ | | 1250 |
| 9 | $7.5 \times 10^{-9}$ | $1.2 \times 10^{-8}$ | 667 (1250) |

3) Action on serum lipoproteins and other metabolic parameters of male rats in the subchronic test Method:

Groups of male rats of the strain HOE: WISKf (SPF 71) having a starting weight of above 180 g received the test preparations daily in the morning (sodium salts of the dihydroxycarboxylic acids of the formula II) in polyethylene glycol 400 by stomach tube; the respective control group received only the vehicle. The last (7th) administration was carried out 24 hours before taking blood and sacrificing. There was free access to food and water during the experiment. 24 hours before taking blood, which wall carried out retroorbitally under slight ether anesthesia before and after the treatment period (i.e. on the 1st and 8th day), the food was withdrawn. Total cholesterol was determined in the serum of each individual animal [CHOD-PAP high performance method of Boehringer Mannheim], and, as a measure of the triglycerides, total glycerol was also determined analytically from the serum pool of all the animals of one group [GPO-PAP high performance method, Boehringer Mannheim].

Immediately after taking blood, the animals were sacrificed by dislocation of the spine, and the relative liver weight, the change in body weight and the food consumption were determined.

For the analysis of the serum lipoproteins, the serum of all the rats of one group was pooled. The serum lipoproteins were separated using the preparative ultracentrifuge.

The following conditions were used for the separation of the fractions VLDL, LDL and HDL:

| | |
|---|---|
| 1. VLDL | density <1.006 |
| 2. LDL | density 1.006 to 1.04 |
| 3. HDL | density 1.04 to 1.21 |
| 4. Subnatant of the HDL (VHDL) | density >1.21 |

The determination of the protein was carried out by the method of Lowry et al. [LOWRY O. H., ROSEBOROUGH, N.J., PARR, A. L. and RANDELL, R. J.: J. Biol. Chem. 193, 265 (1951)].

ylcellulose (®Tylose MH 300), 5.10 or 20 mg/kg/day daily in the morning by stomach tube. The animals of the control groups received only Tylose MH 300. Every 3-4 days samples of venous blood were taken from all animals 20 hours after the oral administration. The serum total cholesterol was determined enzymatically in these samples using the test combination of Boehringer Mannheim (CHOD-PAP high performance method). The serum cholesterol level of the treated animals was compared with that of the control groups. A "discharge phase" followed the 20-day "treatment phase", in which the change in the serum cholesterol level was further monitored.

Before, three times during the treatment phase and in the discharge phase, the safety parameters (SGOT, SGPT, aP, bilirubin and creatinine in the serum) of the animals in the control group and in the treated groups were also determined. They showed no significant changes.

Before, six times during the treatment phase and in the discharge phase, the body weight of the animals in the control group and in the treated groups was also determined. No significant change took place compared to the starting ($\pm 1\%$).

| Test compound | Dose mg/kg per day | Serum total cholesterol % change compared to control group | | | | | | | |
|---|---|---|---|---|---|---|---|---|---|
| | | Number of administration | | | | | Discharge phase | | |
| | | 3 | 10 | 14 | 17 | 20 | 3 | 6 | 11 | 22 |
| Ex. 1 | 5 mg (constant) | −44 | −46 | −43 | −42 | −48 | −22 | −17 | −6 | — |
| Ex. 9 | 5 mg (constant) | −8 | −12 | −15 | — | — | −4 | −4 | +6 | — |
| Compound C | 10 mg (up to 10th day) | +7 | −32 | | | | | | | |
| | 20 mg (from 11th day) | | | −31 | −37 | −36 | −13 | −23 | −16 | +18 |
| Mevinolin | 10 mg (up to 10th day) | −12 | −30 | | | | | | | |
| | 20 mg (from 11th day) | | | −27 | −24 | −26 | +14 | −1 | +2 | 0 |

From Table 4, it can be seen that the compound from Example 1 causes a substantially greater plasma cholesterol decrease than mevinolin or the compound C in spite of lower dosage. Furthermore, it can be seen that the action of the compound from Example 1 commences very early on. The maximum action was virtually achieved even in the first measurement after 3 days of treatment.

TABLE 3

| Test substance Example | Dose mg/kg | % change compared to control | | | | | | % changes in the mean value | | | |
|---|---|---|---|---|---|---|---|---|---|---|---|
| | | Total cholesterol | | | Protein | | Glycerol | Relative to control | | Relative to starting values | Cholesterol |
| | | VLDL | LDL | HDL | VLDL | LDL | VLDL | Liver weight | Food consumption | Body weight | HDL/LDL* |
| 7 | 100 | −23 | −52 | +9 | −15 | −8 | −3 | −1 | ±0 | +5 | 2.25 |
| 6 | 100 | +13 | −16 | −3 | −2 | +3 | −8 | +1 | −1 | +5 | 1.15 |
| 6 | 30 | +12 | −26 | +13 | −4 | −24 | +8 | +3 | −1 | +5 | 1.27 |
| Standard clofibrate | 100 | −40 | −19 | −29 | −16 | −9 | +4 | +15 | +1 | +8 | 0.88 |
| Standard probucol | 30 | +4 | −24 | −11 | −6 | −23 | +24 | +5 | ±0 | +5 | 0.97 |
| None (control) | — | — | — | — | — | — | — | — | — | +4 | 1.00* |

*Control standardization to 1.00

4) Hypocholesterolemic activity in rabbits after p.o. administration

Normolipemic male white New Zealand rabbits, body weight 3-3.5 kg, were divided into groups of 5 animals. The groups in each case received one of the test compounds (sodium salts of the compounds of the formula II), suspended in 1% aqueous meth- 5) Inhibition of microsomal lipid peroxidation (in vitro)

The inhibition of lipid peroxidation was measured under the experimental conditions described by H. Wafers and H. Sies, Eur. J. Biochem. 174, 353–357 (1988). The microsomes were obtained according to the literature cited therein. $IC_{50}$ denotes the concentration of the test compound in moles per liter which causes a 50% inhibition of lipid peroxidation.

TABLE 5

| Process/Example | Example | $IC_{50}$ | Inhibition at $10^{-5}$ mol/l |
|---|---|---|---|
| 4 | | $4.4 \times 10^{-6}$ | 90% |
| 5 | | — | 11% |
| 6 | | $3.0 \times 10^{-6}$ | 95% |
| 7 | | $4.0 \times 10^{-6}$ | 92% |
| 8 | | — | 1% |
| 12 | | $1.5 \times 10^{-6}$ | 99% |
| 22 | | $1.6 \times 10^{-6}$ | 99% |
| 23 | | $2.8 \times 10^{-6}$ | 98% |
| 25 | | $4.8 \times 10^{-6}$ | 83% |
| | 1 | — | <10% |
| | 2 | — | <10% |
| | 5 | — | 0% |
| | 6 | $2.7 \times 10^{-6}$ | 98% |
| | 7 | — | <10% |
| | 8 | — | 27% |
| | 9 | — | <10% |

6) Inhibition of $Cu^{2+}$-catalyzed LDL oxidation in vitro LDL was isolated from porcine plasma which contained EDTA (1 mg/ml) by ultracentrifugation in salt solutions of NaCl/NaBr between the densities 1.019 and 1.063 g/ml (cf. R. J. Havel et al., J. Clin. Invest. 43, 1345 (1955)). LDL was then dialyzed against phosphate-buffered saline (160 mM NaCl, 10 mM $NaH_2PO_4$), pH 7.4 and stored under nitrogen at 4° C. Before the oxidation process, the LDL fractions were diluted to a final protein concentration of 0.1 mg/ml using phosphate-buffered saline and 2.5 ml aliquot parts were pre-incubated under nitrogen with the test compounds (25 μl of ethanolic solution) for 1 hour at 37° C. (cf. McLean et al., Biochemistry 1989, 28, 321). For the $Cu^{2+}$-catalyzed oxidation of LDL, 12.5 μl of a 1 mM $CuSO_4$ solution were added to each sample, a 5 μM $Cu^{2+}$ concentration resulting. The incubation was carried out for 2 hours at 37° C. and in an air atmosphere. The fluorescence intensity was measured at 430 nm (excitation wavelength 365 nm) (cf. Steinbrecher, U. P., J. Biol. Chem. 1987, 262, 3603). The $IC_{50}$ value (concentration of the test compound in mol per liter which causes a 50% inhibition of LDL oxidation) was determined from the decrease in the relative fluorescence intensity ($LDL_{OX}=100$). The values are compiled in Table 6. In addition, the inhibition using a $10^{-5}$N concentration of the test compound is indicated in %.

TABLE 6

| Process Example | Example | $IC_{50}$ μmol/l | Inhibition at $10^{-5}$ M |
|---|---|---|---|
| 6 | | 1.0 | |
| 25 | | 0.15 | |
| | 1 | >10 | 41% |
| | 8 | 1.1 | |
| | 9 | 6.0 | |
| | 10 | >10 | 23% |
| Standard probucol | | 0.50 | |

In the following process examples, the synthesis of precursors which are required for the preparation of the compounds of the formulae I and II according to the invention is described. In the examples, the preparation of compounds of the formulae I and II according to the invention, their esters and salts is described. The process examples and the examples do not have a limiting character on the scope of the invention.

General Experimental Technique

Reactions were carried out in glass apparatuses under a nitrogen inert gas atmosphere. If not stated otherwise, technical-grade solvents were used for reactions and chromatography without further purification or drying. Reagents had a purity of at least 97% (usually >99%). Drying of reaction extracts was carried out, if not stated otherwise, with magnesium sulfate. Thin-layer chromatographic analyses (TLC) were carried out on prepared silica gel 60 glass TLC plates containing fluorescent indicator $F_{254}$ (Merck). The detection of the product spots was carried out by means of UV, and by the use of spray reagents for staining.

Column chromatographic separations were carried out in glass columns and under conditions such as have been described for flash chromatography [W. C. Still et al., J. Org. Chem. 43, 2923 (1978)]. Silica gel of particle size 35–70 Mm, pore diameter 60 Å or 70–200 μm, pore diameter 60 Å from Amicon, was used.

$^1$H-NMR spectra were recorded using a ®Bruker WP60 or WM270 spectrometer. If not stated otherwise, $CDCl_3$ was used as the solvent. Chemical shifts are indicated in ppm, relative to tetramethylsilane as internal standard.

Mass spectra were recorded using a ®Kratos MS9 (FAB) or MS80 (CI) spectrometer.

Melting points were determined using a Büchi capillary melting point apparatus (according to Dr. Tottoli) and are uncorrected.

PROCESS EXAMPLE 1

2-Bromo-6-isopropylphenol (scheme 1, formula Viii)

198.1 ml (3.85 mol) of bromine were added dropwise at −5° to 0° C. to a solution of 470 g of sodium hydroxide in 2 l of water. The mixture was stirred at this temperature for a further 10 min. The resulting sodium hypobromite solution was added dropwise at −5° to 0° C. to a solution of 464 g of a 40% strength aqueous dimethylamine solution (4.11 mol) in 50 ml of water. The mixture was stirred for a further 30 min, the organic phase was then separated off and the aqueous phase was extracted twice using 750 ml of methylene chloride each time. The combined organic phases were dried briefly over magnesium sulfate and filtered. The filtrate was added dropwise at −10° C. to a solution of 500 g (3.67 mol) of ortho-isopropylphenol in 900 ml of methylene chloride. After adding about ⅔ of the filtrate, a solid formed and the reaction mixture became viscous and could only be stirred with difficulty. 500 ml of methylene chloride were added at −10° C. and the mixture was stirred for a further hour. The solid was filtered off with suction, washed with a little cold methylene chloride, suspended in 1.5 l of 2N sulfuric acid and stirred at room temperature until all the solid had been converted into an oil. The organic phase was separated off, and the aqueous phase was extracted using methylene chloride. The combined organic phases were washed with sodium chloride solution and dried, and the solvent was removed in vacuo. The residue was distilled through a 30 cm Vigreux column in a water jet vacuum.

391.7 g (1.82 mol) of colorless oil, b.p. 122°–124° C./21 torr; yield 49.6%

NMR (60 MHz): δ=1.20 (d, 6H, CH₃), 3.23 (sept., 1H, CH), 5.42 (s, 1H, OH), 6.4–7.2 (m, 3H, arom. H).

PROCESS EXAMPLE 2

2-(p-Fluorophenyl)-6-isopropylphenol (scheme 1, formula IX)

a) Three iodine crystals were added to 18.7 g (0–77 mol) of magnesium turnings and the site of addition was heated with a hot air apparatus (®Fön) until iodine vapor was visible in the flask. The mixture was cooled to room temperature and 20 ml of absolute THF were added. 131.3 g (0.75 mol) of p-bromofluorobenzene were poured into a 500 ml dropping funnel and about 2 ml thereof were added to the reaction flask. The brown color of the reaction mixture rapidly disappeared and strong evolution of heat took place to reflux. A further 50 ml of absolute THF were immediately added to the reaction mixture and the p-bromofluorobenzene in the dropping funnel was diluted with 200 ml of THF. This solution was then added dropwise in such a way that a gentle reflux was maintained. The reaction mixture was subsequently boiled under reflux for a further hour and then cooled to 50° C.

b) In a second flask, the dissolved oxygen was driven off from the solution of 52.0 g (0.24 mol) of 2-bromo-6-isopropylphenol in 150 ml of absolute THF by means of introducing nitrogen for 20 minutes. 1.7 g (1.5 mmol) of tetrakis(triphenylphosphine)palladium(O) were added with minimization of oxygen contact.

The Grignard solution from step a) was then transferred to this solution under nitrogen pressure by means of a double needle ("®Flex-Needle", Aldrich), evolution of heat occurring. The speed of the transfer was chosen so that a gentle reflux was maintained. The mixture was subsequently heated to reflux for a further 6 hours. The reaction mixture was cooled and poured onto 500 g of ice/100 ml of conc. hydrochloric acid. The organic phase was separated off and the aqueous phase was extracted using 3×100 ml of ether. The combined organic phases were washed with 100 ml of saturated sodium chloride solution and dried, and the solvent was stripped off. The residue was distilled through a 30 cm Vigreux column under a pump vacuum. After a forerun (30°–65° C./0.2 torr), the pure product distilled (b.p. 107°–109° C./0.5 torr) as a colorless oil which crystallized in the receiver and partly also even in the distillation bridge (m.p. 44°–46° C.). In order to avoid blocking of the bridge, this was temperature-controlled to about 50° C. Yield 37.8 g of title compound (164 mmol); 68.4% of theory. GC analysis (30 m fused silica column DB-5 "polydiphenyldimethylsiloxane", layer thickness 0.25 μm, internal diameter 0.32 m, 180° C., injector 240° C., 1 bar of H₂): t_ret: 4.46 min; purity>99.9%.

NMR (270 MHz): δ=1.28 (d, 6H, CH₃) 3.32 (sept., 1H, CH), 5.08 (s, 1H, OH), 6.9–7.5 (m, 7H, arom. H).

MS (DCI, isobutane): m/e=231 (M+H⁺), 230 (M⁺), 215 (M⁺—CH₃),.

PROCESS EXAMPLE 3

2-(p-Fluorophenyl)-4-thiocyanato-6-isopropylphenol (scheme 1, formula X)

A suspension of 70.9 g (838 mmol, 5.0 equivalents) of sodium thiocyanate in 200 ml of methanol was stirred at room temperature for 20 min. 40.0 9 (173.8 mmol, 1.0 equiv.) of 2-(p-fluorophenyl)-6-isopropylphenol were added and the mixture was stirred for 20 minutes. 14.32 ml (277.8 mmol, 1.6 equiv.) of bromine were dissolved in 50 ml of methanol (exothermic) and this solution was added dropwise at 15°-20° C. to the above reaction solution during the course of 20 minutes. The reaction mixture turned yellow and the phenol dissolved completely. The reaction mixture was stirred for 30 min. TLC (toluene/cyclohexane 1:1) showed complete conversion of the starting material (R_f=0.54). In addition to the title compound (R_f=0. 32), only a small amount of the corresponding para-bromo compound, which cochromatographed with the starting material (R_f=0. 54), was obtained as an impurity, but was able to be differentiated owing to different coloration. The reaction mixture was poured onto 400 g of ice/400 ml of 2N hydrochloric acid and extracted using 4×200 ml of toluene. The extracts were washed with aqueous sodium sulfite solution, filtered, washed with saturated sodium chloride solution, dried and concentrated in vacuo.

The yellow solid which remained was dissolved in 500 ml of hot cyclohexane and 5 g of active carbon were added. The mixture was then heated under reflux for 5 minutes and the hot suspension was filtered in vacuo. The active carbon filtered off with suction was subsequently washed with 20 ml of hot cyclohexane. The almost colorless filtrate cooled slowly and was then cooled to 10° C. for a further 12 hours.

The colorless crystals (title compound) were filtered off with suction and dried in vacuo. 47.6 g (165.7 mmol) yield corresponding to 95.3%; m.p.: 94.5°–96° C.

NMR (60 MHz): δ=1.26 (d, 6H, CH₃), 3.32 (sept., 1H, CH), 5.46 (s, 1H, OH), 7.0–7.6 (m, 6H, arom. H).

MS (DCI, isobutane): m/e=288 (M+H⁺), 272 (M⁺—CH₃), 261 (M⁺—CN)

PROCESS EXAMPLE 4

2-(P-Fluorophenyl)-4-mercapto-6-isopropylphenol (scheme 1, formula III/2)

A solution of 32.5 g (113 mmol) of 2-(p-fluorophenyl)-4-thiocyanato-6-isopropylphenol in 150 ml of absolute THP was added dropwise to a suspension of 7.5 g (198 mmol) of lithium aluminum hydride in 20 ml of absolute THF. The reaction mixture was heated under reflux for 90 min. TLC (CH/EA 9:1; R_f of the thiocyanate: 0.16; R_f of the mercaptan: 0.26) indicated quantitative reaction. 100 ml of conc. hydrochloric acid were cautiously added dropwise to the mixture with dry ice-cooling. The aluminum salts went into solution during the course of this. The reaction mixture was extracted several times with ether. The combined extracts were washed with saturated sodium chloride solution and dried, and the solvents were removed in vacuo. The residue was filtered through a silica gel column under nitrogen pressure using the above eluent. 27.3 g (104 mmol) of the pure product (title compound) were obtained as a colorless oil (yield: 92.1%).

NMR (60 MHz): δ=1.27 (d, 6H, CH₃), 3.30 (sept., 1H, CH), 3.40 (s, 1H, SH), 5.06 (s. 1H. OH), 6.93–7.63 (m, 6H, arom. H).

MS (DCI, isobutane) : m/e=262 (M⁺), 247 (M⁺—CH₃).

IR (CHCl₃): 3555 (OH), 2560 (weak, SH), 1510, 1455, 1223, 840 cm⁻¹.

The product is sensitive to oxidation and must be handled with rigorous exclusion of oxygen.

PROCESS EXAMPLE 5

4,4-(Isopropylidenedithio)-bis-[(2-isopropyl-6-p-fluorophenyl)phenol] (scheme 1, formula III/3)

27.3 g (104 mmol) of 2-(p-fluorophenyl)-4-mercapto-6-isopropylphenol were dissolved in 100 ml of benzene which had been previously freed of oxygen by means of bubbling nitrogen through. 13.5 g (16 ml, 130 mmol) of 2,2-dimethoxypropane, followed by about 100 mg (~0.5 mmol) of p-toluenesulfonic acid monohydrate were added. The reaction mixture was stirred at room temperature for 30 min, then under reflux for 8 hours. It was washed with aqueous sodium acetate solution, then with saturated sodium chloride solution, dried and concentrated in vacuo. The oil which remained (29.0 g) was chromatographed on silica gel using cyclohexane/toluene 1:1+1 part per thousand triethylamine and gave 26.0 g of title compound (46.0 mmol, yield 88.5%) as a yellowish oil which crystallized in the refrigerator. It melted close to room temperature.

NMR (60 MHz): $\delta = 1.28$ (d, 12H, C(CH$_3$)$_2$), 1.53 (s, 6H, —S—C(CH$_3$)$_2$—S), 3.32 (sept., 2H, CH), 5.26 (s,, 2H, OH), 7.0–7.7 12H, arom. H)

MS (FAB, 3-NBA/LiI): m/e571 (M+Li$^+$), 303

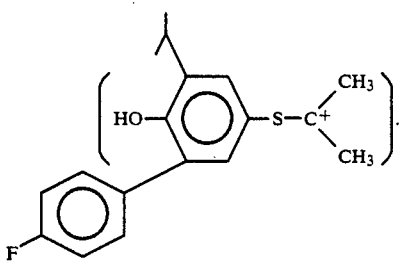

PROCESS EXAMPLE 6

2-(p-Fluorophenyl)-4-(p-fluorophenylthio)-6-isopropylphenol (scheme 1, formula III/1)

A THF solution (100 ml) of p-fluorophenylmagnesium bromide [from 3.11 9 (128 mmol) of magnesium and 22.0 g (13.8 ml, 126 mmol) of p-bromofluorobenzene] was prepared as in Process Example 2. A solution of 6.04 g (21 mmol) of 2-(p-fluorophenyl)-4-thiocyanato-6-isopropylphenol (from Process Example 3) in 50 ml of THF was added dropwise at 50° C. and stirred at 40°-50° C. for a further 2 hours. The mixture was cooled and poured onto 500 ml of ice-cold 2N hydrochloric acid. The mixture was extracted three times using 200 ml of ether. The combined extracts were washed with sodium chloride solution and dried, and the solvent was removed in vacuo.

The oil which remained (title compound) (7.5 g, 21 mmol, yield ~100%) was pure according to TLC (cyclohexane/ethyl acetate 9:1) and $^1$H-NMR.

NMR (60 MHz): $\delta = 1.25$ (d, 6H, CH$_3$), 3.31 (sept., 1H, CH), 5.22 (s, 1H, OH), 6.8–7.8 (m, 10H, arom. H).

MS (DCI, isobutane): m/e=357 (M+H$^+$), 356 (M$^+$).

PROCESS EXAMPLE 7

2-(p-Fluorophenyl)-4-(phenylthio)-6-isopropylphenol (scheme 1, formula III/1)

In analogy to Process Example 6, the action of 6 equivalents of phenylmagnesium bromide on 2-(p-fluorophenyl)-4-thiocyanato-6-isopropylphenol (from Process Example 3) in THF at 40°-50° C. gave the title compound in 95% yield.

NMR (60 MHz): $\delta = 1.25$ (d, 6H, CH$_3$) 3.30 (sept., 1H, CH), 5.20 (s, 1H, OH), 6.9–7.8 (m, 11H, arom. H).

MS (DCI, isobutane): m/e=339 (M+H$^+$), 338 (M$^+$).

PROCESS EXAMPLE 8

2-(p-Fluorophenyl)-4-(isopropylthio)-6-isopropylphenol (scheme 1, formula III/1)

910 mg (39.6 mmol) of sodium pieces were added to 20 ml of isopropanol and the mixture was stirred until the metal had completely disappeared. A solution of 2.5 g (8.7 mmol) 3) of 2-(p-fluorophenyl)-4-thiocyanato-6-isopropylphenol (from Process Example 3) in 50 ml of isopropanol was added dropwise to the solution obtain during the course of one hour. The reaction mixture was heated under reflux for 30 min, then poured into 100 ml of 2N sulfuric acid and extracted using 3×100 ml of ether. The combined extracts were washed with saturated sodium chloride solution, dried and concentrated in vacuo. The oil residue (2.42 g) was chromatographed using cyclohexane/ethyl acetate 2:1, later 1:1 and yielded 640 mg (2.1 mmol, yield 24.1%) of a viscous, yellowish oil (title compound).

NMR (60 MHz): $\delta = 0.97$ (d, 6H, SC(CH$_3$)$_2$), 1.20 (d, 6H, C(CH$_3$)$_2$)3.00–3.90 (2 x sept., 2H, CH), 5.20 (s, 1H, OH), 6.9–7.7 (m, 6H, arom. H).

MS (DCI, isobutane): m/e=305 (M+H$^+$), 304 (M$^+$).

PROCESS EXAMPLE 9

2-Bromo-6-cyclopropylphenol (scheme 1, formula VIII)

In analogy to Process Example 1, the title compound was obtained from ortho-cyclopropylphenol [Y. S. Shaborov, V. K. Potapov and R. Y. Levina, J. Gen. Chem. USSR 34, 3171 (1964)]in 384 yield as a colorless oil.

NMR (60 MHz): $\delta = 0.73$ (m, 4H, CH$_2$), (qui, 1H, CH), 5.42 (s, 1H, OH), 6.4–7.2 (m, 3H, arom. H).

MS (DCI, isobutane): m/e=213/215 (M+H$^+$), 212/214 (M$^+$).

PROCESS EXAMPLE 10

2-(p-Fluorophenyl)-6-cyclopropylphenol (scheme 1, formula IX)

In analogy to Process Example 2, the title compound was obtained from 2-bromo-6-cyclopropylphenol in 47% yield as a colorless solid.

NMR (60 MHz): $\delta = 0.78$ (m, 4H, CH$_2$), 1-85 (qui, 1H, CH), 5.00 (s, 1H, OH), 6.7–7.5 (m, 7H, arom. H).

MS (DCI, isobutane): m/e=229 (M+H$^+$), 228 (H$^+$).

PROCESS EXAMPLE 11

2-(p-Fluorophenyl)-4-thiocyanato-6-cyclopropylphenol (scheme 1, formula X)

In analogy to Process Example 3, the title compound was obtained from 2-(p-fluorophenyl)-6-cyclopropylphenol in 62% yield as a pale yellow solid (m.p. 82°–85 0c).

NMR (60 MHz): $\delta = 0.79$ (m, 4H, CH$_2$), 1.88 (qui, 1H, CH), 5.36 (B, 1H, OH), 6.9–7.6 (m, 6H, arom. H).

MS (DCI, isobutane): m/e=286 (M+H$^+$), 259 (M$^+$—CN).

PROCESS EXAMPLE 12

2-(p-Fluorophenyl)-4-(p-fluorophenylthio)-6-cyclopropylphenol (scheme 1, formula III/1)

In analogy to Process Example 6. the title compound was obtained from 2-(p-fluorophenyl)-4-thiocyanato-6-cyclopropylphenol as a viscous, pale yellow oil.

NMR (60 MHz): $\delta = 0.78$ (m, 4H, $CH_2$), 1.87 (qui, 1H, CH), 5.12 (s, 1H, OH), 6.7–7.7 (m, 10H, arom. H).

MS (DCI, isobutane): m/e=355 (M+H+), 354 (M+).

PROCESS EXAMPLE 13

2-(p-Fluoro-m-methylphenyl)-6-isopropylphenol (scheme 1, formula IX)

In analogy to Process Example 2, the title compound was obtained from 2-bromo-6-isopropylphenol (from Process Example 1) and the Grignard reagent from p-fluoro-m-methylbromobenzene in 68% yield as a colorless solid.

NMR (60 MHz): $\delta = 1.25$ (d, 6H, $CH_3$), 2.35 (s, 3H, $CH_3$), 3.30 (sept., 1H, CH), 5.00 (s, br, 1H, OH), 6.7–7.5 (m, 6H, arom.

MS (DCI, isobutane): m/e=245 (M+H+), 244 (M+), 229 (M+—$CH_3$).

PROCESS EXAMPLE 14

2-(p-Fluoro-m-methylphenyl)-4-thiocyanato-6-isopropylphenol (scheme 1, formula X)

In analogy to Process Example 3, the title compound was obtained from 2-(p-fluoro-m-methylphenyl)-6-isopropylphenol in a 59% yield as a pale Yellow solid (m.p. 96°–98° C.).

NMR (60 MHz): $\delta = 1.26$ (d, 6H, $CH_3$), 2.35 (s, 3H, $CH_3$), 3.32 (sept., 1H, OH), 5.47 (s, 1H, OH), 7.0–7.6 (m, 5H, arom. H).

MS (DCI, isobutane): m/e=302 (M+H+), 286 (M+—$CH_3$), 275 (M+—CN).

PROCESS EXAMPLE 15

2-(p-Fluoro-m-methylphenyl)-4-(p-fluorophenylthio)-6-isopropylphenol (scheme 1, formula III/1)

In analogy to Process Example 6, the title compound was obtained from 2-(p-fluoro-m-methylphenyl)-4-thiocyanato-6-isopropylphenol as a viscous, pale yellow oil.

NMR (60 MHz): $\delta = 1.25$ (d, 6H, $CH_3$), 2.34 (s, 3H, $CH_3$), 3.31 (sept., 1H, CH), 5.23 (s, 1H, OH), 6.8–7.8 (m, 9H, arom. H).

MS (DCI, isobutane): m/e=371 (M+H+), 370 (M+).

PROCESS EXAMPLE 16

1-Acetyl-2,5-diisopropylbenzene (scheme 3, formula XIV)

A solution of 142 ml (157 g, 2.0 mol) of acetyl chloride in 362 ml (310 g, 1.91 mol) of 1,4-diisopropylbenzene was added dropwise during the course of 2 hours to a suspension of 200 g (1.5 mol) of aluminum trichloride in 260 ml of carbon disulfide cooled to −10° C. The mixture was stirred for a further 1.5 hours at −100° C., in the course of which the evolution of hydrogen chloride greatly decreased, and a further 100 g (0.75 mol) of aluminum trichloride were then added in portions and the mixture was stirred for a further hour. The reaction mixture was cautiously poured onto 1 kg of ice/100 ml of 2N hydrochloric acid (strongly exothermic?). The oily organic phase was separated off and the aqueous phase was extracted twice using ether. The combined organic phases were washed with dilute sodium carbonate solution, then with water and dried over calcium chloride. The solvents were stripped off and the residue was distilled through a 30 cm Vigreux column in a pump vacuum. After a forerun (b.p. 70°–91° C./ 0.6 torr, colorless oil, 10.9 g), the title compound (b.p. 92°–95° C./0.6 torr, colorless oil, 344.3 g, 1.69 mol), was obtained, yield 88.4%. The afterrun (b.p. 97°–104° C./1.0 torr, 10.25 g) is a colorless oil which immediately solidifies.

The product is pure according to TLC (cyclohexane/ethyl acetate 5:1, $R_f = 0.45$).

PROCESS EXAMPLE 17

1-(2-Hydroxy-2-propyl)-2,5-diisopropylbenzene (scheme 3, formula XV)

197 g (0.97 mol) of 1-acetyl-2,5-diisopropylbenzene were added dropwise to 468 ml (1.4 mol) of a commercial 3-molar solution of methylmagnesium iodide in ether in such a way that a gentle reflux was maintained. The mixture was heated under reflux for a further one hour, then poured cautiously onto 1.5 l of ice-cold, aqueous ammonium chloride solution, and the organic phase was separated off and extracted twice more using ether. The combined organic phases were washed with saturated sodium chloride solution and dried, and the solvent was removed in vacuo.

213.1 g (yield 100%) of a viscous oil (TLC: cyclohexane/ethyl acetate 5:1, $R_f = 0.26$) were obtained. Pure 1-(2- hydroxy-2-propyl)-2,5-diisopropylbenzene can be obtained from this crude product by crystallization from about 400 ml of petroleum ether at −20° C. The crystal formation frequently requires several days.

NMR (60 MHz): $\delta = 1.25$ (d, 12H, $CH_3$), 1.68 (s, 6H, $CH_3$), 1.74 (s, 1H, OH), 2.86 (sept., 1H, CH), 3.82 (sept., 1H, CH), 6.96–7.42 (m, 3H, arom. H).

It is advantageous to react the crude alcohol further directly.

PROCESS EXAMPLE 18

1,2,5-Triisopropylbenzene (scheme 3, formula XVII)

The crude alcohol from Process Example 17 (213.1 g, 0.97 mol) was heated under reflux in a water separator with 800 ml of toluene and two spatula tips full of para-toluenesulfonic acid hydrate. 15 ml of water were separated in the course of 1 hour. TLC (100% toluene) showed complete reaction of the alcohol (R.=0.17) to the olefin ($R_f = 0.79$). The toluene was removed in vacuo at a bath temperature of 20° C. The oily residue was dissolved in 160 ml of n-hexane. 4.7 g of 10% palladium on carbon were added under nitrogen and the mixture was shaken at room temperature under a hydrogen atmosphere of 1 atm. 21.2 l of hydrogen were absorbed in the course of 12 hours. The catalyst was filtered off with suction through kieselguhr (for example ®Celite) and washed with n-hexane. The filtrate was concentrated in vacuo at a bath temperature of 20° C. The oily residue was distilled through a 30 cm Vigreux column in a water jet vacuum. The distillate in the boiling range 70°–128° C./12 torr (178.5 g) was collected in fractions. All fractions contained the product ($R_f = 0.65$) according to TLC analysis (100% cyclohexane) in addition to a polar impurity ($R_f = 0.05$), the content of which increased with progressive distillation. The impurity was removed by column chromatography (100% cyclohexane).

166.2 g (0.81 mol) of the title compound were obtained as a colorless oil. Yield 83.8%.

NMR (60 MHz): δ=1.18 (d, 18H, CH$_3$), 2.63-3.60 (3 x sept., 3H, CH), 6.87-7.30 (m, 3H, arom. H).

MS (DCI, isobutane): m/e=205 (M+H+), 204 (M+), 189 (M+—CH$_3$).

GC (30 m fused silica column DB-5 "polydiphenyldimethylsiloxane", layer thickness 0.25 μm, internal diameter 0.32 mm, 160° C., injector 240° C., 1 bar of helium): t$_{ret}$ 4.39 min, purity 97.1%.

PROCESS EXAMPLE 19

1-Bromo-2,4,5-triisopropylbenzene (scheme 3, formula XVIII)

A spatula tip full of iron powder was added at −10° C. to a solution of 301.3 g (1.47 mol) of 1,2,5-triisopropylbenzene in 600 ml of carbon tetrachloride and a solution of 76 ml (236.2 g, 1.48 mol) of bromine in 600 ml of carbon tetrachloride was then added dropwise with rigorous exclusion of light. Initially, no noticeable evolution of hydrogen bromide took place and the bromine color of the reaction solution remained. After complete addition, the mixture was allowed to warm to 0° C., whereupon a vigorous evolution of hydrogen bromide commenced. The mixture was stirred for a further 90 min At room temperature, after which TLC (100% cyclohexane) indicated extensive disappearance of the starting material (R$_f$=0.51) (product R$_f$=0.57; by-product R$_f$=0.64).

The reaction solution was partitioned between methylene chloride and 10% strength sodium thiosulfate solution. The organic phase was separated off and the aqueous phase was extracted once more with methylene chloride. The combined organic phases were washed with sodium chloride solution, dried and concentrated in vacuo. The oily residue was fractionated through a 20 cm Vigreux column in a pump vacuum:

1) forerun, 5.3 g of colorless oil, b.p. 71°-103° C./1 torr
2) main run, 265.4 g (0.94 mol) of the title compound, b.p. 105°-112° C./1 torr, very pale yellow oil, yield 64.0%
3) after-run 35.8 g of yellow oil, b.p. 114°-120° C./1 torr, title compound + by-product.

GC of the main run (column DB-5, conditions as in Process Example 18): t$_{ret}$ 8.81 min, purity: 98.4%.

NMR (60 MHz) 1.24 (d, 18H, CH$_3$ 3.19 (sept., 1H, CH), 7.12 (s, 1H, arom. H), 7.33 (s, 1H, arom. H).

MS (PCI, isobutane): m/e=285/283 (M+H+), 284/282 (M+), 269/267 (M+—CH$_3$), 243/241 (M+—Λ.)

PROCESS EXAMPLE 20

1-(p-Fluorophenyl)-2,4,5-triisopropylbenzene (scheme 3, formula XIX)

A few crystals of iodine were added to 22.3 g (0.92 mol) of magnesium turnings and the mixture was heated using a hot air apparatus (®Fön) until violet iodine vapor was formed. About 50 ml of absolute THF were added, followed by about 20 ml of a total of 251 g (0.89 mol) of 1-bromo-2,4,5-triisopropylbenzene. As soon as the reaction had started (heating to reflux may be necessary), 150 ml of absolute THF were added through the reflux condenser, the residual bromine compound was diluted in the dropping funnel with about 300 ml of THF and this solution was added dropwise in such a way that a gentle reflux was maintained. After complete addition, the mixture was heated for a further 30 min under reflux and a clear, slightly greenish solution was obtained, which was cooled to about 40° C.

In a second apparatus, the oxygen was driven out of a solution of 162.6 g (0.93 mol) of 4-bromofluorobenzene in 800 ml of absolute THF by bubbling nitrogen through (30 min). 10 g (8.6 mmol) of tetrakis(triphenylphosphine)palladium(O) were added and the solution was stirred at room temperature for 10 min. The above Grignard solution was then transferred to this solution under pressure by means of a double needle using nitrogen (about 15 min). The mixture was heated under reflux for 2 hours, whereupon a white precipitate deposited from the initially clear reaction solution. The reaction mixture was allowed to cool and poured into ether and 2N hydrochloric acid, the precipitated magnesium bromide being largely removed by decanting. The organic phase was separated off and washed successively with 2N hydrochloric acid, water, saturated sodium hydrogen carbonate solution and saturated sodium chloride solution, then dried, filtered and concentrated in vacuo.

The residue was distilled in a pump vacuum without a column and using a short, air-cooled bridge. After a forerun (25.5 g, b.p. 25°-101° C./0.15 torr), the product (187.5 g, 628 mmol, b.p. 114° C./0.05 torr) distilled and immediately crystallized to give a colorless, hard solid (title compound) (m.p. 75°-78° C.).

NMR (60 MHz): δ=1.10-1.36 (3 xd, 18H, CH$_3$)2.80-3.56 (m, 3H, CH), 6.86-7.40 (m, 6H, arom. H).

MS (DCI, isobutane): m/e=299 (M+H+), 298 (M+), 257 (M+—C$_3$H$_5$).

PROCESS EXAMPLE 21

2-(p-Fluorophenyl)-3,5,6-triisopropyl-1,4-benzoquinone (scheme 3, formula XX)

60.0 g (201 mmol) of 1-(p-fluorophenyl)-2,4,5-triisopropylbenzene were introduced into a 2 l flask containing a mechanical stirrer, efficient reflux condensers dropping funnel, internal thermometer and inert gas inlet/bubble counter. A solution of 68 ml of 70% strength aqueous hydrogen peroxide in 333 ml of trifluoroacetic acid was added dropwise at −20° C. The cooling bath was removed, but was kept ready for immediate use again. The reaction mixture warmed to about +20° C. in the course of 30 min. A very exothermic reaction commenced at this temperature, control of which required immediate cooling with a dry ice cooling bath. Despite this cooling, the reaction mixture warmed to reflux. The cooling was then controlled in such a way that a slight reflux was maintained. After 10-15 min, the exothermic reaction decreased and TLC (cyclohexane/toluene 1:1) showed the complete reaction of the starting material (R$_f$=0.72) to give the yellow reaction product (R$_f$=0.45) and polar byproducts.

The reaction mixture was cautiously poured into ice-cold sodium hydrogen carbonate solution and extracted 3 times using ether. The combined ether phases were washed twice with sodium hydrogen carbonate solution, then with sodium chloride solution, dried and concentrated. The residue was chromatographed through silica gel using cyclohexane/toluene 2:1 and gave 14.6 g (44.5 mmol, yield 22.1%) of an intensively yellow solid (title compound), m.p. 122°-124° C.

According to $^1$H-NMR and MS, the title compound prepared in this way contained about 10% of an impurity (MW=344) which could not be separated by chromatography.

NMR (270 MHz): δ=1.15–1.40 (m, 18H, CH$_3$), 1.98 (sept., 1H, CH), 2.63 (sept., 1H, CH), 3.24 (sept., 1H, CH), 7.08 (AA'BB' system, 4H, arom. H).

MS (CDI, isobutane): m/e=329 (M+H$^+$).

PROCESS EXAMPLE 22

2-(p-Fluorophenyl)-3,5,6-triisopropyl-1,4-hydroquinone (scheme 3, formula III/4)

6.3 g (166.5 mmol) of sodium borohydride were added at room temperature under nitrogen to a solution of 11.1 g (33.8 mmol) of the quinone from Process Example 21 in 740 ml of ethanol. After stirring for one hour, decolorization of the yellow solution occurred. The ethanol was removed in vacuo and the mixture was aerated with nitrogen (on admission of oxygen reoxidation of the hydroquinone formed takes place with yellow coloration). 500 ml of nitrogen-flushed, 2 normal hydrochloric acid were cautiously added to the residue with ice-cooling (vigorous evolution of hydrogen, evolution of heat) and the mixture was shaken with 500 ml of ether which had been decanted from lithium aluminum hydride. The ether phase was separated off, concentrated in vacuo and aerated with nitrogen. The residue was dried in a high vacuum, stirred with n-pentane, filtered off with suction under nitrogen and washed with n-pentane, then dried in a high vacuum. 9.65 g (29.2 mmol, 86.4% yield) of colorless solid (title compound) were obtained, m.p. 193°–196° C.

NMR (270 MHz): δ=1.23 (d, 6H, CH$_3$), 1.34 (d, 6H, CH$_3$), 1.42 (d, 6H, CH$_3$), 2.66 (sept., 1H, CH), 3.40–3.70 (s, very broad, probably limited rotation of the isopropyl groups, 2H, CH), 4.12 (s, 1H, OH), 4.39 (s, 1H, OH), 7.12–7.28 (m, 4H, arom. H).

MS (DCI, isobutane): m/e=330 (M$^+$).

PROCESS EXAMPLE 23

2,5,6-Triisopropyl-3-(p-fluorophenyl)-4-acetoxyphenol (scheme 3, formula III/5)

1.73 ml (18.34 mmol, 1.5 equiv.) of acetic anhydride, followed by 23 ml of degassed, dry pyridine, were added with ice-cooling to 4.04 g (12.23 mmol) of the hydroquinone from Process Example 22. The reaction mixture was allowed to stand at 0° C. under argon and with exclusion of moisture in a refrigerator for 3 days. TLC (cyclohexane/diisopropyl ether 4:1) showed extensive reaction of the starting material (R$_f$=0.60) and formation of the title compound (R$_f$=0.36) as the main product, in addition to the diacetate (scheme 3, formula XXI) (R$_f$=0.21) and the regioisomeric monoacetate (scheme 3, formula III/6) (R$_f$=0.41) as by-products. The reaction mixture was poured into 200 ml of 2N hydrochloric acid and 500 ml of ether and the mixture was shaken. The ether phase was washed successively with 100 ml of 2N hydrochloric acid twice, 100 ml of sodium hydrogen carbonate solution and 50 ml of saturated sodium chloride solution, dried, filtered and concentrated.

The residue (4.10 g) was dissolved in a little toluene with warming, and this solution was applied to a silica gel column and eluted with cyclohexane/diisopropyl ether 5:1. After a little starting material (200 mg, 0.61 mmol), initially 150 mg (0.40 mol) of 2.3,5-triiso propyl-4-acetoxy-6-(p-fluorophenyl)phenol (scheme 3, formula III/6) were eluted, followed by 2.14 g (5.75 mmol, yield 47.0%) of the title compound, followed by 940 mg (2.27 mmol) of 1,4-diacetoxy-2,3,5-triisopropyl-6-(p-fluorophenyl)benzene (scheme 3, formula XXI).

Total yield of all acetylation products, relative to unreacted starting material, 72.5%.

The title compound was obtained as a colorless solid, m.p. 192°–195° C.

NMR (60 MHz): δ=1.15–1.53 (3 xd, 18H, CH$_3$), 1.72 (s, 3H, CO—CH$_3$), 2.3–3.8 (m, 3H, CH), 4.81 (s, 1H, OH), 6.98–7.26 (AA'BB'-system, 4H, arom. H), MS (DCI, isobutane): m/e=373 (M+H$^+$), 372 (M$^+$), 330 (M+H$^+$—CH$_3$CO).

PROCESS EXAMPLE 24

1,4-Diacetoxy-2,3,5-triisopropyl-6-(p-fluorophenyl)-benzene (scheme 3, formula XXI)

3.46 ml (36.7 mmol, 3.0 equiv.) of acetic anhydride, followed by 23 ml of dry pyridine, were added with ice-cooling to 4.04 g (12.23 mmol) of the hydroquinone from Process Example 22. The reaction was carried out, and the product was worked up and purified by chromatography as indicated in Process Example 23. In addition to small amounts of the regioselective monoacetates, 3.06 g (8.22 mmol, yield 67.2%) of the title compound were obtained as a colorless solid, m.p. 172°–173° C.

NMR (60 MHz): δ=0.9–1.6 (m, 18H, CH$_3$, hindered rotation), 1.70 (s, 3H, CO—CH$_3$)1 2.35 (s, 3H, CO—CH$_3$), 2.43–3.73 (m, 3H, CH), 6.97–7.20 (AA'BB'-system, 4H, arom. H).

MS (DCI, isobutane): m/e=415 (M+H$^+$), 414 (M$^+$), 373 (M+H$^+$—CH$_2$=C=O) 372 (M$^+$—CH$_2$=C=O), 331 (M+H$^+$—2 CH$_2$=C=O) 330 (M$^+$—2 CH$_2$=C=O).

PROCESS EXAMPLE 25

2,3,5-Triisopropyl-4-acetoxy-6-(p-fluorophenyl)phenol (scheme 3, formula III/6)

A solution of 114.2 mg (4.77 mmol, 1.1 equivalents) of lithium hydroxide in 9.83 ml of water was added to a solution of 1.8 g (4.34 mmol) of the diacetate from Process Example 24 in 30 ml of 1,2-dimethoxyethane. The reaction mixture was stirred at room temperature. After a short time, a colorless solid precipitated, and after stirring for 3 days, a clear solution was obtained. TLC (cf. Process Example 20) showed only traces of the diacetate, and the title compound as the main product in addition to the regioisomeric monoacetate as a by-product.

The reaction mixture was poured into 2N hydrochloric acid and extracted using ether. The extract was washed with sodium hydrogen carbonate solution and then with saturated sodium chloride solution, dried and concentrated. Column chromatography (cf. Process Example 23) gave 980 mg (2.63 mmol, 60.6% yield) of the title compound as a colorless solid, m.p. 174°–177° C. In addition, 480 mg (1.29 mmol, 29.7% yield) of a compound which was identical to that from Process Example 23 were obtained.

NMR (60 MHz): δ=0.85–1.53 (m, 18H, CH$_3$), hindered rotation), 2.32 (s, 3H, CO—CH$_3$), 2.40–3.65 (m, 3H, CH), 4.40 (s, 1H, OH), 7.0–7.36 (m, 4H, arom. H).

PROCESS EXAMPLE 26 tert.-Butyl (3R,5S)-6-methylsulfonyloxy-3,5-O-isopropylidene-3,5-dihydroxyhexanoate (formula IV)

116.2 g (1.01 mol, 1.5 equiv.) of methanesulfonyl chloride were added dropwise at 0°–5° C. to a solution of 175.7 g (676 mmol) of tert.-butyl (3R,5S)-6-hydroxy-3,5-O-isopropylidene-3,5-dihydroxyhexanoate (see EPA 0,319,847) in 1.7 l of absolute methylene chloride and 1.7 l of absolute pyridine. The reaction mixture was stirred with ice-cooling for 90 min., and it was then concentrated in vacuo at 30° C. and the major amount of the residual pyridine was removed by stripping off in vacuo after taking up in toluene. The residue was taken up in toluene and the solution was washed twice with water, once with saturated sodium hydrogen carbonate solution and once with saturated sodium chloride solution, then dried, filtered and concentrated in vacuo. The oil which remained crystallized virtually completely at room temperature within a few minutes. The crystals were filtered off with suction, powdered on the suction filter, washed with cold petroleum ether and dried in vacuo.

192.0 g (568 mmol) of colorless solid; m.p. 75°–76° C., were obtained. Concentrating the filtrate, filtering off the crystals with suction and washing with a little cold petroleum ether yielded a further 34.8 g (103 mmol) of slightly impure product, m.p. 69°–73° C. Total yield of title compound: 226.8 g (671 mmol, 99.3%).

NMR (270 MHz, $CD_2Cl_2$): $\delta=1.18$–1.33 (m, 1H, $CH_2$, axial), 1.36 (s, 3H, $CH_3$) 1.42 (s, 9H, tert.-Bu), 1.46 (s, 3H, $CH_3$) 11.56 (dt, 1H, $CH_2$, equatorial), 2.36 (AB part of ABX system, 2H, $CH_2$), 3.03 (s, 3H, $CH_3$—$SO_2$), 4.09–4.23 (m, 3H, $OCH_2$ and O—CH), 4.24–4.37 (m, 1H, OCH).

MS (DCI, isobutane): m/e=283 (M+H+—>=).

PROCESS EXAMPLE 27

(2,2-Dimethyl-4(S)-[(2-p-fluorophenyl-4-p-fluorophenylthio-6-isopropyl)phenoxymethyl]-6(R)-tert.-butoxycarbonylmethyl}-1,3-dioxolane (formula V)

2.02 g (14.6 mmol, 1.3 equiv.) of powdered potassium carbonate and about 10 mg of crown ether 18-crown-6 (Aldrich) were added to a solution of 4.0 g (11.2 mmol) of 2-(p-fluorophenyl)-4-p-fluorophenylthio)-6-isopropylphenol (Process Example 6) in 25 ml of dry hexamethylphosphoramide (HMPT). The suspension was stirred at room temperature for 20 min, then 4.55 g (13.5 mmol, 1.2 equiv.) of tert.-butyl (3R,5S)-6-methylsulfonyloxy-3,5-O-isopropylidene-3,5-dihydroxyhexanoate (Process Example 26) were added and the mixture was stirred at 75°–80° C. for 2 days. The reaction mixture became dark-colored and more viscous. It was poured into 200 ml of aqueous sodium dihydrogen phosphate solution and extracted several times using ether. The combined extracts were washed with saturated sodium chloride solution, dried and concentrated in vacuo and gave 8.64 g of a brownish oil.

Column chromatography (cyclohexane/ethyl acetate 10:1 plus 1 part per thousand of triethylamine) gave 4.96 g (8.28 mmol, 74.0% yield) of a pale yellow, viscous oil (title compound).

NMR (270 MHz, $C_6D_6$): $\delta=0.98$–1.07 (m, 2H, $CH_2$), 1.19+1.20 (2 xd, 6H, $CH(CH_3)_2$), 1.38 (s, 9H, tert.-Bu), 1.39+1.41 (2xs, 6H, $OC(CH_3)_2$), 2.12 (dd, 1H, $CH_2CO_2$), 2.42 (dd, 1H, $CH_2CO_2$), 3.27 (dd, 1H, O-$CH_2$), 3.37 (dd, 1H, O—$CH_2$) 3.65 (sept., 1H, $CH(CH_3)_2$), 3.65–3.76 (m, 1H, O—CH), 4.10–4.21 (m, 1H, O—CH), 6.60+6.82 (AA′BB′ system, 4H, arom. H), 7.12–7.18 (m, 2H, arom. H), 7.22–7.29 (m, 3H, arom. H), 7.45 (d, 1H, arom. H).

MS (DCI, isobutane): m/e=598 (M+), 543 (M+H+—>=), 485.

PROCESS EXAMPLE 28 tert.-Butyl 3(R),5(S)-dihydroxy-6-[(2-p-fluorophenyl-4-p-fluorophenylthio-6-isopropyl)phenoxy]hexanoate (formula II/1)

A solution of 4.47 g (7.47 mmol) of the acetonide from Process Example 27 in 50 ml of tetrahydrofuran, 50 ml of ethanol and 5 ml of 2N hydrochloric acid was stirred at room temperature for 16 hours. TLC (cyclohexane/ethyl acetate 1:1) showed nearly quantitative conversion of the starting material ($R_f=0.78$) to the product ($R_f=0.59$). The reaction mixture was poured into aqueous sodium hydrogen carbonate solution and extracted several times using ether. The extracts were washed with saturated sodium chloride solution, dried and concentrated in vacuo. The residue (4.46 g of brownish oil) was purified by column chromatography (cyclohexane/ethyl acetate 2:1) and gave 3.37 g (6.03 mmol) of title compound as a colorless oil (yield 80.8%).

NMR (270 MHz, $C_6D_6$): $\delta=1.1$–about 1.4 (m, partially covered by strong singlets, 2H, $CH_2$) 1.18 (d, 6H, $CH(CH_3)_2$), 1.31 (s, 9H, tert.-Bu), 2.00 (dd, 1H, $CH_2$—$CO_2$) 2.13 (dd, 1H, $CH_2$—$CO_2$), 3.15 (s, broad, 1H, OH), 3.36 (AB part of ABX systems, 2H, $OCH_2$), 3.52 (s, broad, 1H, OH), 3.56 (sept., 1H, $CH(CH_3)_2$), 3.76–3.96 (m, 2H, 2 x CHOH), 6.61+6.79 (AA′BB′ system, 4H, arom. H), 7.14–7.27 (m, 5H, arom. H), 7.45 (d, 1H, arom. H).

MS (FAB, 3-NBA): m/e=558 (M+), 519, 503 (M+—>=+H+), 356 (M+ of the phenol building block).

PROCESS EXAMPLE 29

{2,2-Dimethyl-4(S)-[(2-p-fluorophenyl-4-p-fluorophenylthio-6-cyclopropyl)phenoxymethyl]-6(R)-tert.-butoxycarbonylmethyl}-1,3-dioxolane (formula V)

In analogy to Process Example 27, 2.44 g (4.09 mmol, 73.0% yield) of the title compound were obtained as a pale yellow, viscous oil from 2.0 g (5.6 mmol) of 2-(p-fluorophenyl)-4-(p-fluorophenylthio)-6-cyclopropylphenol (Process Example 12).

NMR (270 MHz, $C_6D_6$): $\delta=0.78$ (m, 4H, $CH_2$), 1.98–1.07 (m, 2H,, $CH_2$)1 1.38 (8, 9H, tert.-Bu), 1.39+1.41 (2 xs, 6H, $OC(CH_3)2$), 1.87 (qui, 1H, CH), 2.13 (dd, 1H, $CH_2CO_2$), 2.42 (dd, 1H, $CH_2CO_2$), 3.32 (AB part of ABX system, 2H, $OCH_2$) 3.64–3.77 (m, 1H, O—CH), 4.10–4.22 (m, 1H, O—CH), 6.61+6.83 (AA′BB′system, 4H, arom. H), 7.10–7.30 (m, 5H, arom. H), 7.46 (d, 1H, arom. H).

MS (DCI, isobutane): m/e=596 (M+), 541 (M+H+—>=).

PROCESS EXAMPLE 30 tert.-Butyl 3(R),S(S)-dihydroxy-6-[(2-p-fluorophenyl-4-p-fluorophenylthio-6-cyclopropyl)phenoxy]hexanoate (formula II/1)

In analogy to Process Example 28, 1.64 g (2.95 mmol, 72.1% yield) of the title compound were obtained as a colorless, viscous oil from 2.44 g (4.09 mmol) of the acetonide from Process Example 29.

NMR (270 MHz, $C_6D_6$) 0.77 (m, 4H, $CH_2$) 1.10–1.35 (m, partially covered, 2H, $CH_2$) 1 1.31 (s, 9H, tert.-Bu), 1.87 (qui, 1H, CH), 1.95–2.18 (AB part of ABX system, 2H, $CH_2CO_2$—), 3.15 (s, broad, 1H, OH), 3.37 (AB part of ABX system, 2H, $OCH_2$), 3.53 (s, broad, 1H, OH), 3,75–3.97 (m, 2H, CHOH), 6.61+6.80 (AA'BB' system, 4H, arom. H), 7.13–7.28 (m, 5H, arom. H), 7.45 (d, 1H, arom. H).

MS (FAB, 3-NBA): m/e=556 ($M^+$), 354 ($M^+$ of the phenol building block).

PROCESS EXAMPLE 31

{2,2-Dimethyl-4(S)-[[2-(p-fluoro-a-methylphenyl)-4-p-fluorophenylthio-6-isopropyl]phenoxymethyl]-6(R)-tert.-butoxycarbonylmethyl}-1,3-dioxolane (formula V)

In analogy to Process Example 27, 5.15 g (8.41 mmol, 74.1% yield) of the pure title compound were obtained as a colorless, viscous oil from 4.2 g (11.35 mmol) of 2-(p-fluoro-m-methylphenyl)-4-(p-fluorophenylthio)-6-isopropylphenol (Process Example 15) and 4.55 g (13.5 mmol) of the mesylate (Process Example 26) after chromatography.

NMR (270 MHz, $C_6D_6$): δ=0.97–1.09 (m, 2H, $CH_2$), 1.20 (d, finely split, 6H, $CH(CH_3)_2$), 1.38 (s, 9H, tert.-Bu), 1.39–1.41 (2 xs, 6H, $OC(CH_3)_2$), 2.13 (dd, 1H, $CH_2CO_2$), 2.35 (s, 3H, $CH_3$), 2.43 (dd, 1H, $CH_2CO_2$), 3.28 (dd, 1H, O—$CH_2$), 3.38 (dd, 1H, O-$CH_2$) 3.65 (sept., 1H, $CH(CH_3)_2$), 3.65–3.76 (m, 1H, O—CH), 4.09–4.22 (m, 1H, O—CH), 6.60–7.44 (m, 9H, arom. H).

MS (DCI, isobutane): m/e=612 ($M^+$), 557 ($M+H^+->=$).

PROCESS EXAMPLE 32 tert.-Butyl 3(R),5(S)-dihydroxy-6-[(2-p-fluoro-m-methylphenyl-4-p-fluorophenylthio-6-isopropyl)phenoxy]hexanoate (formula II/1)

In analogy to Process Example 28, 3.70 g (6.47 mmol, yield 77.7%) of colorless oil were obtained from 5.10 g (8.33 mmol) of the acetonide from Process Example 31 after chromatography.

MS (FAB, 3-NBA): m/e=572 ($M^+$), 517 ($M^+->=+H^+$), 370 ($M^+$ of the phenol building block).

PROCESS EXAMPLE 33

{2,2-Dimethyl-4(S)-[(2-p-fluorophenyl-4-phenylthio-6-isopropylphenoxymethyl ]-6 (R) -tert.-butoxycarbonylmethyl}-1,3-dioxolane (formula V)

In analogy to Process Example 27, 5.4 g (9.31 mmol, 67.0% yield) of a colorless, viscous oil were obtained from 4.7 g (13.90 mmol) of 2-p-fluorophenyl-4-phenylthio-6-isopropylphenol (Process Example 7) after chromatography.

NMR (270 MHz, $C_6D_6$): δ=0.97–1.08 (m, 2H, $CH_2$), 1.20 (2 xd, 6H, $CH(CH_3)_2$), 1.37 (s, 9H, tert.-Bu), 1.39+1.41 (2 xs, 6H, $OC(CH_3)_2$), 2.13 (dd, 1H, $CH_2CO_2$), 2.42 (dd, 1H, $CH_2CO_2$), 3.32 (AB part of ABX system, 2H, $OCH_2$) 3.66 (sept., 1H, $CH(CH_3)$ 2), ~3.65–3.77 (m, 1H, O—CH), 4.09–4.22 (m, 1H, O—CH), 6.62–7.28 (m, 11H, arom. H).

MS (DCI, isobutane): m/e=580 ($M^+$), 525 ($M+H^+->=$), 467.

PROCESS EXAMPLE 34 tert.-Butyl 3(R),5(S)-dihydroxy-6-[(2-p-fluorophenyl-4-phenylthio-6-isopropyl)-phenoxy]hexanoate (formula II/1)

In analogy to Process Example 28, 3.65 g (6.76 mmol, yield 73.3%) of colorless, viscous oil were obtained from 5.35 g (9.2 mmol) of the acetonide from Process Example after chromatography.

MS (FAB, 3-NEA): m/e=540 ($M^+$), 501, 485 ($M^+->=+H^+$), 338 ($M^+$ of the phenol building block).

PROCESS EXAMPLE 35

(2,2-Dimethyl-4(S)-[(2-p-fluorophenyl-4-isopropylthio-6-isopropylphenoxymethyl]-6(R)-tert.-butoxycarbonylmethyl}-1,3-dioxolane (formula V)

A suspension of 206 mg (0.68 mmol) of 2-(p-fluorophenyl)-4-(isopropylthio)-6-isopropylphenol (Process Example 8), 271 mg (0.80 mmol) of tert.-butyl (3R,5S)-6-methylsulfonyloxy-3,5-O-isopropylidene-3.5-dihydroxyhexanoate (Process Example 26), 221 mg (1.60 mmol) of powdered potassium carbonate and a microspatula tip full (1–2 mg) of crown ether 18-crown-6 in 6.8 ml of dry hexamethylphosphoramide was heated at 65°–70° C. for 12 hours, then at 80° C. for a further 6 hours. TLC (cyclohexane/ethyl acetate 5:1) showed complete conversion of the starting phenol. The reaction mixture was cooled, poured into sodium hydrogen carbonate solution and extracted twice using ether. The combined ether phases were washed twice with water and once with saturated sodium chloride solution, dried, filtered and concentrated. The residue was chromatographed on silica gel using toluene/ethyl acetate 30:1, later 20:1, and gave:

in fractions 6–8 40.1 mg of an unidentified reaction product, $R_f$(toluene/ethyl acetate, 20:1):0.40, in fractions 10–15 110.3 mg of the title compound, $R_f$: 0.32, pale yellow, viscous oil, in fractions 23–27 32.5 mg of a compound which, on the basis of $^1$H-NMR and MS, is allocated the structure

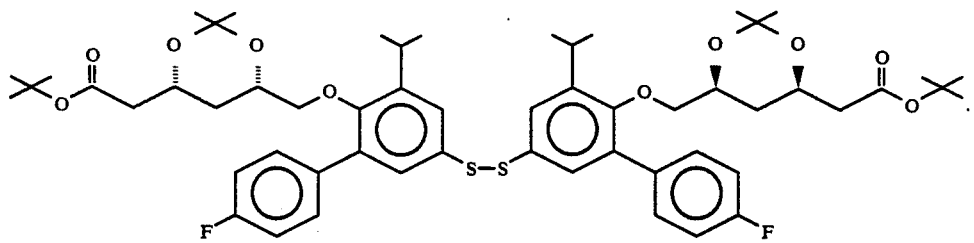

$R_f$: 0.14, pale yellow, viscous oil,
in fractions 30–35 40.7 mg of a compound which, on the basis of $^1$H-NMR and MS, is allocated the structure

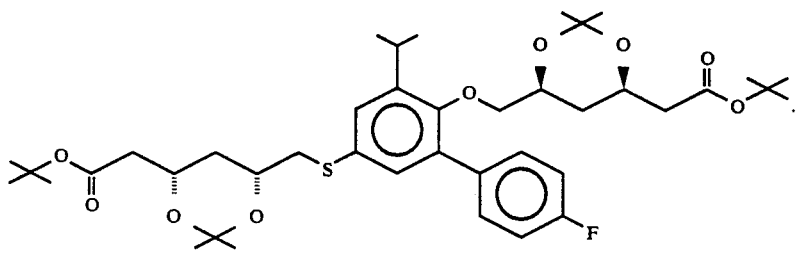

$R_f$: 0.08, pale yellow, viscous oil. Spectra of the title compound (fractions 10–15):

NMR (270 MHz): δ=0.97 (d, 6H, SC(CH$_3$)$_2$), 1.22 (d, finely split, 6H, CH(CH$_3$)$_2$), 1.15–1.33 (m, 1H, CH$_2$), 1.38 (s, 3H, CH$_3$), 1.42 (s, 3H, CH$_3$), 1.45 (s, 9H, tert.-Bu), 1.82 (dt, 1H, CH$_2$), 2.37 (AB part of ABX system, 2H, CH$_2$), 2.87 (dd, 1H, OCH$_2$), 3.09 (dd, 1H, OCH$_2$), 3.45 (sept., 1H, CH), 3.64 (sept., 1H, CH), 4.02 (m, 1H, CH), 4.23 (m, 1H, CH), 7.03–7.53 (m, 6H, arom. H).

MS (DCI, isobutane): m/e=546 (M+), 489 (M+ tert.-Bu), 433.

Spectra of fractions 23–27:

NMR (270 MHz): δ=1.06 (AB system, 4H, CH$_2$), 1.20+1.21 (2 xd, 12H, CH(CCH$_3$)$_2$), 1.32 (s, 6H, C(CH$_3$)$_2$), 1.40 (s, 6H, C(CH$_3$)$_2$), 1.43 (s, 18H, tert.-Bu), 2.33 (AB part of ABX system, 4H, CH$_2$CO$_2$), 3.20–3.51 (m, 6H, OCH$_2$ and CH(CH$_3$)$_2$), 3.89 (m, 2H, CH), 4.19 (m, 2H, CH), 7.00–7.51 (m, 12H, arom. H).

MS (FAB): m/e=1006 (M+), 223.

Spectra of fractions 30–35:

3.47 (sept., 1H, CH(CH$_3$)$_2$), 3.89 (m, 1H, CH), 4.02 (m, 1H, CH), 4.22 (m, 2H, CH), 7.03–7.26 (m, 4H, arom. H), 7.45–7.52 (m, 2H, arom. H).

MS (DCI, isobutane): m/e=748 (M+), 689 (M+-tert.-BU) 577, 519.

PROCESS EXAMPLE 36 tert.-Butyl 3(R),5(S)-dihydroxy-6-[2-p-fluorophenyl-4-isopropylthio-6-isopropyl)phenoxy]hexanoate (formula II/1)

In analogy to Process Example 28, 74 mg of colorless, viscous oil were obtained from 100 mg of the acetonide (Process Example 35, fractions 10–15) after chromatography.

MS (FAB, 3-NBA): m/e=506 (M+), 451 (M+—>=+H+), 304 (M+ of the phenol building block).

PROCESS EXAMPLE 37

<2,2-Dimethyl-4(S)-{2-isopropyl-4-[(3-isopropyl-4-hydroxy-5-p-fluorophenyl-1-phenylthio)-2-propyl-2-thio]-6-p-fluorophenylphenoxymethyl)-6(R)-tert.-butoxycarbonylmethyl>-1,3-dioxolane (scheme 2, formula V/1)

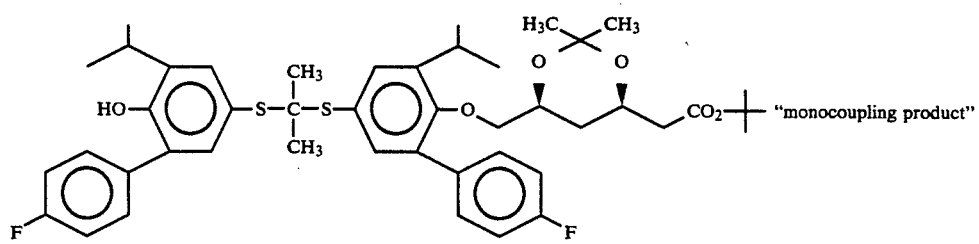

"monocoupling product"

NMR (270 MHz): δ=1.07 (~qua, 1H, CH$_2$), 1.16–~1.30 (covered, 2H, CH$_2$), 1.24 (2 xd, 6H, CH(CH$_3$)$_2$), 1.32 (s, 3H, CH$_3$), 1.37 (s, 3H, CH$_3$), 1.39 (s, 3H, CH$_3$), 1.41 (s, 3H, CH$_3$), 1.43+1.44 (2 xs, 18H, tert.-Bu) 1.80 (dt, 1H, CH$_2$), 2.21–2.48 (2xAB part of ABX system, 4H, CH$_2$CO$_2$), 2.87 (dd, 1H, SCH$_2$), 3.08 (dd, 1H, SCH$_2$), 3.26 (dd, 1H, OCH$_2$), 3.37 (dd, 1H, OCH$_2$)1 and 4,4-(Isopropylidenedithio)-bis-<{1-[(2S,4R)-2,4-O-iso-
propylidene-
2,4-dihydroxy-5tert.-butoxycarbonyl]pentoxy-2-isopro-
pyl-6-p-fluorophenyl}benzene> (scheme 2, formula
XII)

Batch 2: Preferred formation of the double coupling
product

A suspension of 26.0 g (46 mmol) of the phenol (Process Example 5), 15.3 g (110.4 mmol, 1.4 equivalents) of potassium carbonate and 50 mg of 18-crown-6 in 150 ml

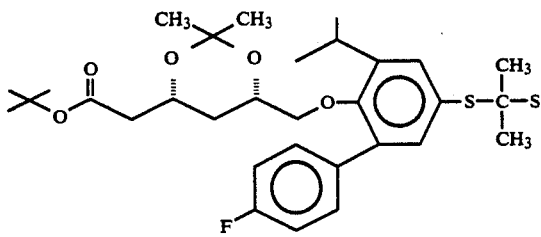
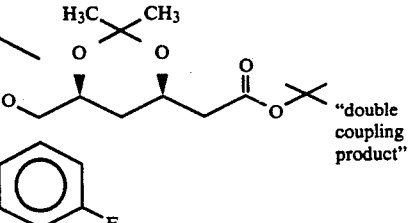

"double coupling product"

Batch 1: Preferred formation of the monocoupling product

A suspension of 4.30 g (7.61 mmol) of 4,4-(isopropylidenedithio)-bis-[-2-isopropyl-6-p-fluorophenyl)-phenol](Process Example 5), 2.50 g (18.09 mmol) of powdered potassium carbonate and 10 mg of crown ether 18-crown-6 in 50 ml of dry HMPT was stirred at room temperature for 30 min. 3.09 g (9.13 mmol, 1.2 equivalents) of tert.-butyl (3R,5S)-6-methylsulfonyloxy-3,5-O-isopropylidene-3,5-dihydroxyhexanoate (Process Example 26) were added and the reaction mixture was stirred at 80°–85° C. for 12 hours. The cooled reaction mixture was poured into 25% strength aqueous sodium dihydrogen phosphate solution and extracted twice using ether. The extracts were washed with saturated sodium chloride solution, dried and concentrated. The residue showed two products ($R_f$=0.34 and 0.26) on TLC analysis (cyclohexane/toluene/ethyl acetate/triethylamine 10:10:1:10$^{-3}$) in addition to a trace of the starting phenol ($R_f$=0.49). Column chromatography on silica gel using this eluent gave 2.598 g (3.22 mmol) of the less polar monocoupling product, yield 42.3%, as a colorless solid, m.p. 47°–50° C. and 1.704 g (1.62 mmol) of the polar double coupling product, yield 21.3%, as a colorless solid, m.p. 48°–51° C.

Spectra of the monocoupling product:

NMR (270 MHz, $C_6D_6$): δ 0.98–1.07 (m, 2H, $CH_2$) 1.24/1.28/1.30 (3 xs, 12H, CH(CH$_3$)$_2$), 1.38 (s, 9H, tert.-Bu), 1.38/1.39 (2 xs, 6H, OC(CH$_3$)$_2$), 1.67 (s, 6H, S—C(CH$_3$)$_2$), 2.12 (dd, 1H, $CH_2CO_2$), 2.42 (dd, 1H, $CH_2CO_2$), 3.22–3.42 (m, 3H, OCH$_2$+CH(CH$_3$)$_2$), 3.62–3.68 (m, 2H, CH+CH(CH$_3$)$_2$), 4.10–4.22 (m, 1H, CH), 6.62–7.15 (m, 6H, arom. H), 7.32–7.41 (m, 2H, arom. H), 7.51/7.67/7.78/7.87 (4 xd, 4 x1H, arom. H).

MS (FAB, 3-NEA/LiI): m/e=813 (M+Li$^+$), 625, 303.

Spectra of the double coupling product:

NMR (270 MHz, $C_6D_6$): δ=0.90–1.08 (m, 4H, $CH_2$), 1.28 and 1.32 (d, 12H, CH(CH$_3$)$_2$), 1.39 (s, 18H, tert.-Bu), 1.40 (2 xs, 12H, OC(CH$_3$)$_2$), 1.66 (s, 6H, S—C(CH$_3$)$_2$—S), 2.12 (dd, 2H, $CH_2CO_2$), 2.43 (dd, 2H, $CH_2CO_2$), 3.27 (dd, 2H, OCH$_2$), 3.39 (dd, 2H, OCH$_2$), 3.63–3.78 (m, 4H, CH(CH$_3$)$_2$ and CH), 4.11–4.23 (m, 2H, CH), 6.82–6.91 (m, 4H, arom. H), 7.32–7.42 (m, 4H, arom. H), 7.68 (d, 2H, arom. H), 7.88 (d, 2H, arom. H).

MS (FAB, 3-NBA/LiI): m/e=1055 (M+Li$^+$), 746, 625, 431, 303.

of dry HMPT were stirred at room temperature for 15 min. 23.3 g (69 mmol, 1.5 equivalents) of the mesylate (Process Example 26) were added and the reaction mixture was stirred at 85° C. for 15 hours. The viscous reaction mixture was diluted with a further 100 ml of HMPT and heated to 85° C. for a further 4 hours. The cooled reaction mixture was poured into 2N hydrochloric acid/ice (1:1), extracted using ether, and the extracts were washed with sodium chloride solution, dried and concentrated. Column chromatography (cyclohexane/toluene/ethyl acetate 30:10:1→10:10:1) gave 11.84 g (31.9% yield) of the monocoupling product and 19.80 g (41.0% yield) of the double coupling product.

PROCESS EXAMPLE 38 tert.-Butyl
3(R),5(S)-Dihydroxy-6-{2-isopropyl-4-[(3-isopropyl-4-hydroxy-5-p-fluorophenyl-1-phenylthio)-2-propyl-2-thiol-6-p-fluorophenylphenoxyyhexanoate (formula II/1)

A solution of 11-84 g (14.7 mmol) of the monocoupling product (Process Example 37, batch 2) in 50 ml of THF, ml of ethanol and 10 ml of 2N hydrochloric acid was stirred at room temperature for 16 hours. The reaction mixture was poured into sodium hydrogen carbonate solution, the mixture was extracted three times with ether and the extracts were washed with sodium chloride solution, dried and concentrated. The residue was chromatographed on silica gel using toluene/ethyl acetate (20:1→5:1) and gave 7.8 g (10.17 mmol, 69.3% yield) of a colorless, viscous Oil.

NMR (270 MHz, $C_6D_6$): δ=1.08–1.22 (m, 2H, $CH_2$), 1.26/1.27 (2 xd, 12H, CH(CH$_3$)$_2$), 1.32 (s, 9H, tert.-Bu), 1.67 (s, 6H, S—C(CH$_3$)2—S), 2.00 (dd, 1H, $CH_2CO_2$), 2.14 (dd, 1H, $CH_2CO_2$), 3.08 (d, 1H, OH), 3.28–3.42 (m, 3H, OCH$_2$ and CH(CH$_3$)$_2$), 3.51 (d, 1H, OH), 3.59 (sept., 1H, CH(CH$_3$)$_2$), 3.77–3.96 (m, 2H, CH), 4.97 (s, 1H, OH), 6.63–6.98 (m, 6H, arom. H) s, 7.32 (m, 2H, arom. H), 7.51/7.67/7.78/7.87 (4 xd, 4 x1H, arom. H).

MS (FAB, 3-NBA/LiI): m/e=773 (M+Li$^+$), 415, 303.

PROCESS EXAMPLE 39

4,4-(Isopropylidenedithio)-bis-<{1-[(2S,4R)@hydroxy-5-tert.-butoxycarbonyl]pentoxy-2-isopropyl-6-p-fluorophenyl}benzene>

A solution of 12.2 g (11.3 mmol) of the double coupling product (Process Example 37, batch 2) in 250 ml of THF, 250 ml of ethanol and 20 ml of 2N hydrochloric acid was stirred at room temperature for 12 hours.

The reaction mixture was poured into aqueous sodium dihydrogen phosphate solution, the mixture was extracted three times using ether and the extracts were washed with sodium chloride solution, dried and concentrated. Column chromatography (silica gel) of the residue using toluene/ethyl acetate 6:1 gave 798 mg (6.8% yield) of a colorless oil, in which only one of the two acetonide groups was hydrolyzed and which had the following formula:

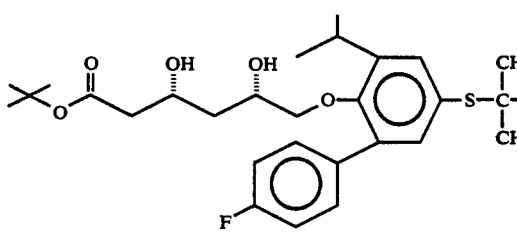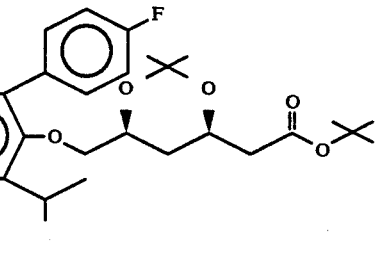

MS (FAB, 3-NEA/LiI): m/e=1015 (M+Li+), 449, 303.

Further elution using methylene chloride/methanol 10:1 gave 8.67 g (77% yield) of the title compound as a viscous oil.

NMR (270 MHz, $C_6D_6$): δ=1.12–1.23 (m, 2H, $CH_2$), 1.28 (d, 12H, CH($CH_3$)$_2$), 1.32 (s, 18H, tert.-Bu), ~1.35–1.42 (m, 2H, $\overline{CH_2}$), 1.66 (s, 6H, S—C($CH_3$)$_2$—S), 2.01 (dd, 2H, $CH_2CO_2$), 2.14 (dd, 2H, $CH_2\overline{CO_2}$), 3.13 (d, 2H, OH), 3.36 (AB part of ABX system, 4H, $OCH_2$), 3.53 (d, 2H, OH), 3.60 (2H, sept., CH($CH_3$)$_2$), 3.78–3.96 (4H, m, CH), 6.82 (m, 4H, arom. H), 7.32 (m, 4H, arom. H), 7.5 6 (d, 2H, arom. H), 7.87 (d, 2H, arom. H).

MS (FAB, 3-NEA/LiI): m/e=975 (M+Li+), 455, 449, 415.

PROCESS EXAMPLE 40

{2,2-Dimethyl-4(S)-[(2,3,5-triisopropyl-4-acetoxy-6-p-fluorophenyl)phenoxymethyl)-6(R)-tert.-butoxycarbonylmethyl}-1,3-dioxolane (formula V)

A suspension of 650 mg (1.75 mmol) of 2,3,5-triisopropyl-4-acetoxy-6-p-fluorophenylphenol (Process Example 25), mg (1.90 mmol) of tert.-butyl (3R,5S)-6-methylsulfonyloxy-3,5-O-isopropylidene-3,5-dihydroxyhexanoate (Process Example 26), 518 mg (3.75 mmol) of potassium carbonate powder and a crystal of 18-crown-6 in 9.6 ml of absolute DMSO were stirred at 70° C. for 12 hours. The suspension became viscous. A further 9.6 ml of DMSO were added and the temperature was increased to 75°–80° C. After 30 min, a further 320 mg (0.95 mmol) of the mesylate and 240 mg (1.75 mmol) of potassium carbonate powder were added. After 10 hours, the reaction mixture was allowed to cool and was poured into aqueous sodium hydrogen carbonate solution, and the mixture was extracted three times using ether. The combined ether phases were washed with sodium hydrogen carbonate solution, then with water and then with NaCl solution, dried, filtered and concentrated. The residue was chromatographed through silica gel 35–70 pm using cyclohexane/ethyl acetate 10:1 +I part per thousand of triethylamine. 770 mg (1.25 mmol, 71.4% yield) of a colorless solid (title compound), m.p. 145°–147° C., were obtained.

NMR (270 MHz, $C_6D_6$): δ=[1.08 (m), 1.22 (d), 1.27 (s), 1.32 (d), 1.41 (s), 1.47 (d), altogether 35H, 3 xCH($\underline{CH_3}$)$_2$), $CH_2$, O—C($CH_3$)$_2$—O, tert.-Bu, obviously hindered rotation of the isopropyl groups], 1.94 (s, 3H, OAc), 2.17 (dd, 1H, $CH_2CO_2$), 2.48 (dd, 1H, $CH_2CO_2$), 3.01 (sept., 1H, C$\underline{H}$($CH_3$)$_2$), 3.2–4.0 (m, 5H, $OCH_2$, CH, 2 xC$\underline{H}$($CH_3$)$_2$, signals of the isopropyl groups very broad, obviously hindered rotation), 4.16 (m, 1H, CH), 6.71–7.28 (m, 4H, arom. H).

MS (DCI, isobutane): m/e=614 (M+), 599 (M+—$CH_3$), 572 (M+—$CH_2$=C=O) 1 559, 557, (M+-tert.-Bu), 501.

PROCESS EXAMPLE 41 tert.-Butyl 3(R),5(S)-dihydroxy-6-[(2,3,5-triisopropyl-4-acetoxy-6-p-fluorophenyl)phenoxy]hexanoate (formula II/1)

A solution of 765 mg (1.15 mmol) of the acetonide (Process Example 40) in 13 ml of ethanol, 13 ml of THF and 1.3 ml of 2N hydrochloric acid was stirred at room temperature for 18 hours. TLC (cyclohexane/ethyl acetate 2:1) showed clean, virtually quantitative reaction of the acetonide ($R_f$=0.63) to give the product ($R_f$=0.26). The reaction mixture was neutralized with potassium hydrogen carbonate powder, ether and water were added and, after vigorously shaking, the ether phase was separated off. It was washed with sodium chloride solution, dried, f altered and concentrated. The residue was chromatographed on silica gel using cyclohexane/ethyl acetate 2:1+1 part per thousand of triethylamine and gave 632 mg (1.10 mmol, 95.6% yield) of colorless solid (title compound), melting point 119°–122° C.

NMR (270 MHz, $C_6D_6$) : δ=0.9–1.5 (m, 29H, 3 xCH($\underline{CH_3}$)$_2$, tert.-Bu, $CH_2$; obviously hindered rotation of the isopropyl groups), 1.93 (s, 3H, OAc), 2.12 (AB part of ABX system, 2H, $CH_2CO_2$, [2.99 (m, 2H) and 3.38–4.12 (m, 7H), 3 xC$\underline{H}$($CH_3$)$_2$1 $OCH_2$, 2 xCH, 2 xOH, obviously hindered rotation of the isopropyl groups], 6.78 (m, 2H, arom. H), 7.03 (m, 2H, arom. H).

MS (DCI, isobutane) m/e=575 (M+H+), 574 (M+), 519 (M+H+—>=), 330 (M+ of the hydroquinone building block).

PROCESS EXAMPLE 42

(2,2-Dimethyl-4(S)-[2,5,6-triisopropyl-3-p-fluorophenyl-4-acetoxyphenoxymethyl]-6(R)-tert.-butoxycarbonylmethyl}-1,3-dioxolane (formula V)

A suspension of 1.28 g (3.4 mmol) of 2,5,6-triisopropyl-3-p-fluorophenyl-4-acetoxy)phenol (Process Example 23), 1.28 g (3.8 mmol) of tert.-butyl (3R,5S)-6-methylsulfonyloxy-3,5-O-isopropylidene-3,5-dihydroxyhexanoate (Process Example 26), 1.02 g (7.6 mmol) of potassium carbonate powder and a crystal of 18-crown-6 in 19 ml of absolute DMSO were stirred at 70° C. for 12 hours, then the temperature was increased to 75°–80° C. After 30 min, a further 575 mg (1.7 mmol) of the mesylate and 470 mg (3.4 mmol) of potassium carbonate powder were added. After 10 hours, the mixture was allowed to cool.

Working up and chromatography were carried out as in Process Example 40. 1.23 g (2.0 mmol, yield 60%) of colorless solid (title compound), melting point 151°–153° C., were obtained.

NMR (270 MHz, $C_6D_6$): $\delta = 1.04$–1.55 [m, 38H, 3 $\times CH(\underline{CH_3})_2$, O—C$(\underline{CH_3})_2$—O, tert.-Bu, $CH_2$, OAc, obviously hindered rotation of the isopropyl groups], 2.22 (dd, 1H, $CH_2CO_2$), 2.51 (dd, 1H, $CH_2CO_2$), 3.39 (m, broad 1H, C$\underline{H}(CH_3)_2$), 3.58 (sept., 1H, C$\underline{H}(CH_3)_2$), 3.71 (AB part of ABX system, 2H, 4.08–4.37 (m, 3H, CH, C$\underline{H}(CH_3)_2$), 6.71–7.42 (m, 4H, arom. H).

MS (DCI, isobutane): m/e=614 (M+), 572; 559, 501.

PROCESS EXAMPLE 43 tert.-Butyl 3(R),5(S)-dihydroxy-6-1(2,5,6-triisopropyl-3-p-fluorophenyl-4-acetoxy)phenoxy]hexanoate (formula II/1)

A solution of 1.22 g (2.0 mmol) of the acetonide (Process Example 42) in 25 ml of ethanol, 25 ml of THF and 2.5 ml of 2N hydrochloric acid was stirred at room temperature for 18 hours. Working up and chromatography as in Process Example 41 gave 1.03 g (1.8 mmol, yield 90%) of the title compound as a colorless solid, melting point 61°–63° C. According to $^1$H-NMR,, this product contained about 5% of an NMR: At 27° C. ($C_6D_6$), most of the signals were broad and complex. In the same solvent at 70° C., the signals were defined: $\delta = 1.17$ (2 xd, 6H, CH($\underline{CH_3})_2$), 1.37 (s, 9H, tert.-Bu), 1.42–1.47 (2 xd+1 xs, 15H, 2 $\times$CH($\underline{CH_3})_2$+OAc), 1.69 (Ab system, 2H, $CH_2$), 2.25 (AB part of ABX system, 2H, $CH_2CO_2$), 3.03 (s, 1H, OH), 3.31 (s, 1H, OH), 3.35 (sept., 1H, C$\underline{H}(CH_3)_2$), 3.56 (sept., 1H, C$\underline{H}(CH_3)_2$), 3.77 (AB part of ABX system, 2H, $OCH_2$), 4.02 (sept., 1H, C$\underline{H}(CH_3)_2$), 4.17 (~qui, 1H, CH), 4.28 (~qui, 1H, CH), 6.83 (m, 2H, arom. H), 6.98–7.17 (m, 2H, arom. H).

MS (DCI, isobutane): m/ep=575 (M+H+), 574 (M+), 519 (M+H+—>=), 330 (M+ of the hydroquinone building block).

EXAMPLE 1

Sodium 3(R),5(S)-dihydroxy-6-[2-p-fluorophenyl-4-p-fluorophenylthio-6-isopropyl)phenoxy]hexanoate (formula II/2)

A suspension of 3.07 g (5.50 mmol) of the tert.-butyl ester (Process Example 28) in 30 ml of ethanol and 5.56 ml (5.56 mmol, 1.01 equivalents) of 1N sodium hydroxide solution was stirred at room temperature for 3 hours. A clear solution was formed during the course of this and TLC (chloroform/methanol 4:1) showed complete reaction of the tert.-butyl ester ($R_f$=0.82) to give the polar product ($R_f$=0.62). The solvents were removed in vacuo. Toluene was twice added to the residue and in each case stripped off in vacuo in order to remove water residues azeotropically. The crystalline residue was washed with cyclohexane, then dried to constant weight in a high vacuum.

2.67 g (93% yield) of a weakly yellow solid (title compound), which melts at 192°–195° C. with decomposition (dark brown coloration), were obtained.

NMR (270 MHz, DMSO-$d_6$): $\delta = 1.18$ (d, 6H, CH($\underline{CH_3})_2$), 1.29 (t, 2H, $CH_2$), 1.40 (s, 1H, OH), 1.77 (dd, 1H, $CH_2CO_2$), 1.99 (dd, 1H, $CH_2CO_2$), 3.21 (AB part of ABX system, 2H, $OCH_2$)1 3.46 (sept., 1H, C$\underline{H}(CH_3)_2$), 3.66 (m, 2H, CH), 4.88 (s, br., 1H, OH), 7.04 (d, 1H, arom. H), 7.18–7.28 (m, 5H, arom. H), 7.37–7.57 (m, 4H, arom. H).

EXAMPLE 2

Sodium 3(R),5(S)-dihydroxy-6-[2-p-fluorophenyl-4-p-fluorophenylthio-6-cyclopropyl)phenoxy]hexanoate (formula II/2)

In analogy to Example 1, 1.25 g of a solid (title compound) which melts at 190°–197° C. with decomposition were obtained from 1.63 g (2.93 mmol) of the tert.-butyl ester (Process Example 30).

NMR (270 MHz, DMSO-$d_6$): $\delta = 0.78$ (m, 4H, $CH_2$), 1.29 (t, 2H, $CH_2$), 1.41 (s, 1H, OH), 1.78 (dd, 1H, $CH_2CO_2$), 1.88 (qui, 1H, CH), 2.00 (dd, 1H, $CH_2CO_2$), 3.22 (AB part of ABX system, 2H, $OCH_2$), 3.67 (m, 2H, CH), 4.89 (s, br., 1H, OH), 7.05 (d, 1H, arom. H), 7.16–7.29 (m, 5H, arom. H), 7.36–7.58 (m, 4H, arom. H).

EXAMPLE 3

Sodium 3(R),5(S)-dihydroxy-6-[2-p-fluoro-a-methylphenyl-4-p-fluorophenylthio-6-isopropyl)phenoxy]hexanoate (formula II/2)

In analogy to Example 1, 3.21 g of colorless solid (title compound) which melts at 197°–201° C. with decomposition were obtained from 3.69 g (6.45 mmol) of the tert.-butyl ester (Process Example 32).

NMR (270 MHz, DMSO-$d_6$): $\delta = 1.19$ (d, 6H, CH($\underline{CH_3})_2$), 1.29 (t, 2H, $CH_2$), 1.41 (s, 1H, OH), 1.78 (dd, 1H, $CH_2CO_2$), 1.98 (dd, 1H, $CH_2CO_2$), 2.35 (s, 3H, $CH_3$), 3.22 (AB part of ABX system, 2H, $OCH_2$), 3.47 (sept., 1H, C$\underline{H}(CH_3)_2$), 3.66 (m, 2H, CH), 4.90 (s, br., 1H, OH), 7.05 (d, 1H, arom. H), 7.17–7.56 (m, 8H, arom. H).

EXAMPLE 4

Sodium 3(R),5(S)-dihydroxy-6-[2-p-fluorophenyl-4-p-phenylthio-6-isopropyl)phenoxy]hexanoate (formula II/2)

In analogy to Example 1, 3.13 g of pale yellow solid (title compound) which melts at 190°–193° C. with decomposition were obtained from 3.64 g (6.74 mmol) of the tert.-butyl ester (Process Example 34).

EXAMPLE 5

Sodium 3(R),S(S)-dihydroxy-6-[(2-p-fluorophenyl-4-isopropylthio-6-isopropyl)phenoxy]hexanoate (formula 11/2)

In analogy to Example 1, 54 mg of yellowish solid (title compound) were obtained from 65 mg (0.13 mmol) of the tert.-butyl ester (Process Example 36).

EXAMPLE 6

Sodium 3(R),5(S)-dihydroxy-6-(2-isopropyl-4-[(3-isopropyl-4-sodio-oxy-5-p-fluorophenyl-1-phenylthio)-2-propyl-2-thio]-6-p-fluorophenylphenoxy)hexanoate (formula II/2)

20.5 ml (20.5 mmol, 2.02 equivalents) of 1N sodium hydroxide solution were added to a solution of 7.8 g (10.17 mmol) of the tert.-butyl ester (Process Example 38) in 75 ml of ethanol and the mixture was stirred at room temperature for 2 hours. TLC (methylene chloride/methanol 10:1) showed complete reaction of the ester ($R_f=0.70$) to give the polar product ($R_f=0.37$). Solvents were removed in vacuo. The residue was taken up in ethanol four times and the solvent was in each case stripped off in vacuo. The residue was washed with cyclohexane, then dried to constant weight in a high vacuum. 7.35 g (9.74 mmol, 95.7% yield) of a yellowish solid (title compound) which begins to melt at 185° C. with decomposition and turns into a black melt at 200°–210° C. were obtained.

NMR (270 MHz, DMSO-$d_6$): $\delta=1.14$ (d, finely split, 6H, CH(CH$_3$)$_2$), 1.22 (d, 6H, CH(CH$_3$)$_2$), 1.32 (t, 2H, CH$_2$), 1.40 (s, 6H, S—C(CH$_3$)$_2$—S), 1.82 (dd, 1H,, CH$_2$CO$_2$), 2.03 (dd, 1H, CH$_2$CO$_2$), 3.15–3.55 (m 6H, OCH$_2$, 2 xOH, 2 xCH(CH$_3$)$_2$), 3.68 (~qui, 2H, CH), 6.86 (d, 1H, arom. H), 7.00 (AA'BB', 2H, arom. H), 7.07 (d, 1H, arom. H), 7.22 (AA'BB', 2H, arom. H), 7.33 (d, 1H, arom. H), 7.50–7.62 (m, 3H, arom. H).

EXAMPLE 7

4,4-(Isopropylidenedithio)-bis-<{1-[(2S,4R)-dihydroxy-5-sodiocarboxy]pentoxy-2-isopropyl-6-p-fluorophenyl}benzene> (formula II/2)

11.4 ml (11.4 mmol, 2.02 equivalents) of 1N sodium hydroxide solution were added to a solution of 5.5 g (5.65 mmol) of the tert.-butyl ester (Process Example 39) in 73 ml of ethanol and the mixture was stirred at room temperature for 2 hours. The solvent was removed in vacuo, and the residue was taken up in methanol five times and the solution was in each case concentrated to dryness in vacuo. The residue was washed with cyclohexane, then dried to constant weight in a high vacuum. 5.08 g (5.64 mmol, 100% yield) of a colorless solid which decomposes at 225°–250° C. with darkening were obtained.

NMR (270 MHz, DMSO-$d_6$): $\delta=1.21$ (d, 12H, CH(H$_3$)$_2$), 1.32 (t, 2H, CH$_2$), 1.50 (s, 6H, S—C(CH$_3$)$_2$—S), 1.78 (dd, 1H, CH$_2$CO$_2$), 2.01 (dd, 1H, CH$_2$CO$_2$), 3.23 (m, 4H, OCH$_2$), 3.39–3.56 (M, 2H, CH(CH$_3$)$_2$), 3.58–3.74 (m, 4H, CH), 4.90 (s, br., 2H, OH), 7.12–7.37 and 7.48–7.62 (m, 12H, arom. H).

EXAMPLE 8

Sodium 3(R),5(S)-dihydroxy-6-[2,3,5-triisopropyl-4-hydroxy-6-p-fluorophenyl)phenoxy]hexanoate (formula II/2)

A suspension of 363 mg (0.63 mmol) of the tert.-butyl ester (Process Example 41) in 3.6 ml of absolute ethanol was cooled in an ice bath and 1.21 ml (1.21 mmol, 2.02 equivalents) of 1N sodium hydroxide solution were added using a syringe. The reaction mixture was stirred at room temperature and rapidly turned into a clear solution. TLC (chloroform/methanol 5:1) after 3 hours showed virtually complete conversion of the starting material ($R_f=0.97$) to product ($R_f=0.28$). The solvents were stripped off, and the residue was taken up toluene twice and in each case concentrated to dryness in vacuo. The residue was washed twice with diisopropyl ether and once with ether, and gave 345 mg of a colorless, fine powder which decomposed and melted at 239°–242° C. while turning brown. This material contained 1 mol equivalent of sodium acetate. Its empirical formula was thus

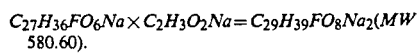

The yield of title compound was 94%.

EXAMPLE 9

Sodium 3(R),5(S)-dihydroxy-6-[2,5,6-triisopropyl-3-p-fluorophenyl)-4-hydroxy)phenoxy]hexanoate (formula II/2)

A suspension of 549 mg (0.96 mmol) of the tert.-butyl ester (Process Example 43,) in 5.8 ml of absolute ethanol was cooled in an ice bath and 1.94 ml (1.94 mmol, 2.02 equiv.) of 1N sodium hydroxide solution were added using a syringe. In contrast to Example 8, the reaction mixture remained a suspension. In spite of this, TLC showed a virtually quantitative conversion after 3 hours. Working up as in Example 8 gave 519 mg of a colorless solid which decomposed and melted at 239°–240° C. while turning brown. This material contained 1 mol equivalent of sodium acetate. Its empirical formula was thus $C_{29}H_{39}FO_8Na_2$ (MW 580.60). The yield of title compound was 93.6%.

EXAMPLE 10

4(R)-Hydroxy-6(S)-[(2-p-fluorophenyl-4-p-fluorophenylthio-6-isopropyl)phenoxymethyl]-3,4,5,6-tetrahydro-2H-pyran-2-one (formula I)

5 ml of trifluoroacetic acid were added dropwise to a solution of 5.59 g (10.2 mmol) of the tert.-butyl ester (Process Example 28) in 20 ml of methylene chloride. The reaction mixture was stirred at room temperature for 2 hours. TLC (cyclohexane/ethyl acetate 1:1) showed quantitative conversion of the tert.-butyl ester ($R_f=0.37$) to the lactone ($R_f=0.12$) and insignificant non-polar impurities. The reaction mixture was neutralized using sodium hydrogen carbonate powder, then rendered neutral using sodium carbonate powder, and then poured into water and extracted several times using ether. The combined organic phases were washed with sodium hydrogen carbonate solution and then with sodium chloride solution, dried, filtered and concentrated. The residue was chromatographed through a silica gel column using cyclohexane/ethyl acetate 1:1 and gave 3.88 g (8.0 mmol, yield 80%) of a colorless solid (title compound), melting point 108°–110° C.

NMR (270 MHz): $\delta=1.30+1.32$ (2 xd, 6H, CH(CH$_3$)$_2$), 1.72–1.94 (m, 3H, CH$_2$ and OH), 2.67 (AB part of ABX system, 2H, CH$_2$CO$_2$), 3.47 (sept., 1H, CH(CH$_3$)$_2$), 3.59 (AB part of ABX system, 2H, OCH$_2$), 4.40 (m, 1H, CH—OH), 4.72 (m, 1H, CH—OCO), 6.80–7.55 (m, 10H, arom. H).

MS (DCI, isobutane): m/e=484 (M+), 467 (M+-OH),

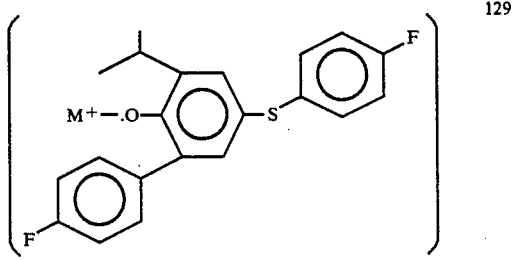

EXAMPLE 11

Sodium 3(R),5(S)-dihydroxy-6-[(2-p-fluorophenyl-4-p-fluorophenylthio-6-isopropyl)phenoxy]hexanoate (formula II/2)

1.0 ml (1.0 mmol) of 1N sodium hydroxide solution was added with ice-cooling to a solution of 485 mg (1.0 mmol) of the lactone (Example 10) in 10 ml of ethanol and the mixture was stirred at 0° C. for 2 hours. The solvents were removed in vacuo. The residue was taken up in toluene twice and the solution was in each case concentrated to dryness in vacuo. The residue was washed with n-pentane and dried to constant weight in a high vacuum. 512 mg (0.98 mmol, 97.6% yield) of a solid (title compound) which is identical with that from Example 1 were obtained.

EXAMPLE 12

4(R)-Hydroxy-6(S)-[(2-p-fluorophenyl-4-p-fluorophenylthio-6-isopropyl)phenoxymethyl]-3,4,5,6-tetrahydro-2H-pyran-2-one (formula I)

1.05 g (2.0 mmol) of the sodium carboxylate (Example 1) were largely dissolved in 32 ml of distilled water. 2 ml of 2N hydrochloric acid (4.0 mmol, 2 equivalents) were added with ice-cooling. The carboxylic acid which precipitated in crystalline form was extracted using ethyl acetate (2×20 ml). The extracts were washed twice with saturated sodium chloride solution, briefly dried, filtered and concentrated in vacuo, and the residue was dried in a high vacuum. Yield 1.00 g (1.99 mmol) of colorless solid. This free carboxylic acid was dissolved in 10 ml of absolute THF and 302 μl (221.5 mg, 2.19 mmol, 1.1 equivalents) of triethylamine were rapidly added dropwise at 0°-10° C., the mixture was stirred at 0° C. for 10 min and then cooled to −10° C., and 200 μl (226.8 mg, 2.09 mmol, 1.05 equivalents) of ethyl chloroformate were slowly added dropwise. The reaction mixture was stirred at −5° C. for 1 hour and partitioned between ether and semi-saturated sodium chloride solution, and the phases were separated. The aqueous phase was extracted two more times using ether and the combined extracts were again washed with sodium chloride solution.

The extracts were dried, filtered and concentrated in vacuo, and the residue was chromatographed through a silica gel column using cyclohexane/ethyl acetate 1:1.

820 mg (1.69 mmol, 85% yield) of a colorless solid (title compound) which was identical with that from Example 10 were obtained.

We claim:
1. A 4-hydroxytetrahydropyran-2-one of formula I

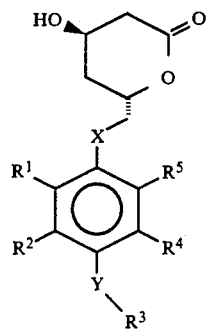

or the corresponding open-chain dihydroxycarboxylic acid of formula II

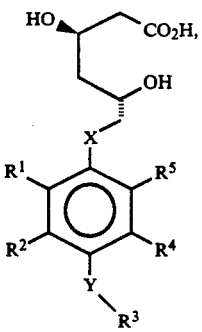

wherein

X is oxygen;

Y is oxygen or sulfur;

$R^1$ is isopropyl or cyclopropyl;

$R^2$ is hydrogen, isopropyl or p-fluorophenyl;

$R^3$ is hydrogen, acetyl, isopropyl, p-fluorophenyl, or one of the radicals

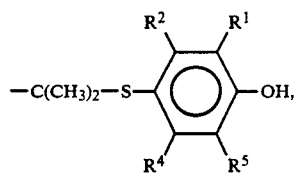

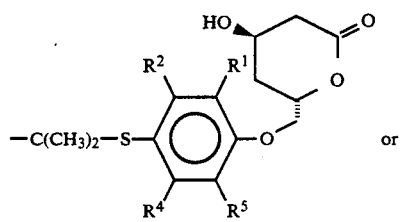

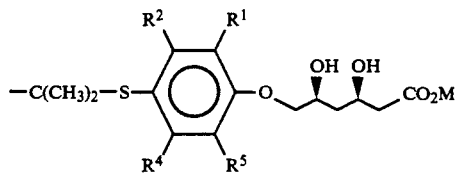

wherein M is hydrogen or sodium;

$R^4$ is hydrogen, isopropyl or p-fluorophenyl; and $R^5$ is isopropyl or p-fluorophenyl;

and pharmaceutically acceptable salt or pharmaceutically acceptable ester thereof.

2. A compound which has one of the following formulae:

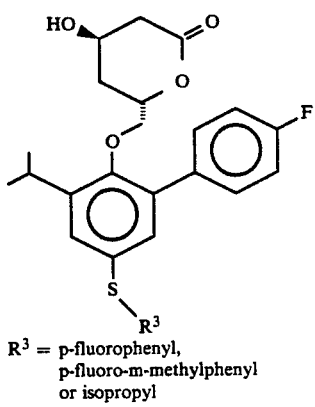

R³ = p-fluorophenyl,
p-fluoro-m-methylphenyl
or isopropyl

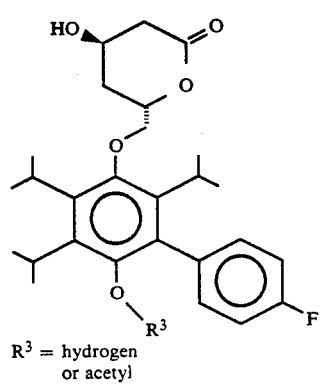

R³ = hydrogen
or acetyl

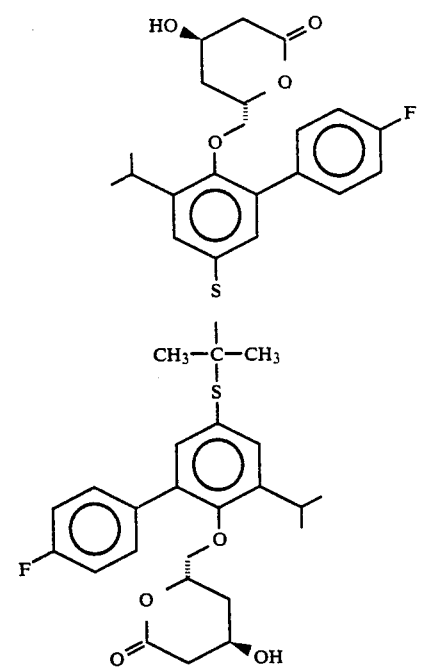

and the corresponding dihydroxycarboxylic acid salts, pharmaceutically acceptable salt or pharmaceutically acceptable ester thereof.

3. A process for the preparation of a compound as claimed in claim 1, which comprises a) reacting appropriately substituted phenols or thiophenols of the formula III

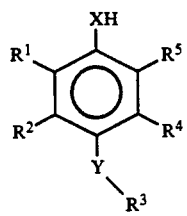

in which X, Y, $R^1$, $R^2$, $R^3$, $R^4$ and $R^5$ have the meanings indicated for formula I, with the optically pure mesylate of the formula IV

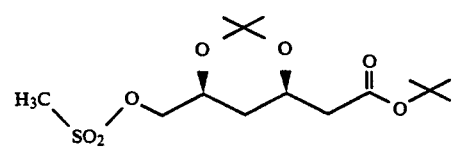

to give the acetonide of the formula V

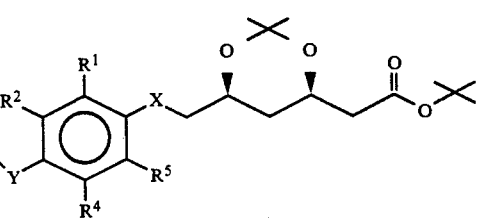

b) converting compounds of the formula V with removal of the protective group into tert.-butyl β,δ-dihydroxycarboxylates of the formula II/1

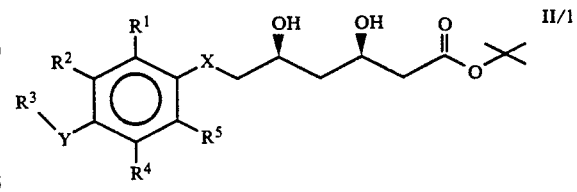

in which X, Y, $R^1$, $R^2$, $R^3$, $R^4$ and $R^5$ have the meanings indicated for formula I, c) hydrolyzing the tert.-butyl esters of the formula II/i to give salts of the formula II/2

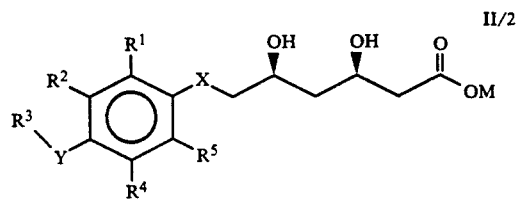

in which X, Y, $R^1$, $R^2$, $R_3$, $R^4$ and $R^5$ have the meanings indicated for formula I and M is a pharmacologically tolerable cation it also being possible to remove protective groups which may be present, d) cyclizing the tert.-butyl esters of the formula II/1 or, if appropriate, the salts of the formula II/2 to the β-hydroxylactones of the formula I

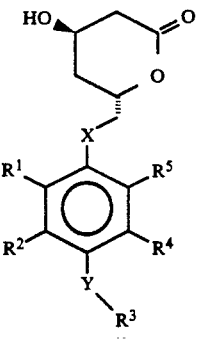

I e) if appropriate converting the hydroxylactones of the formula I into the corresponding open-chain dihydroxycarboxylic acids of the formula II, their salts or their esters, if desired converting the salts or esters into the free dihydroxycarboxylic acids of the formula II or if desired converting the dihydroxycarboxylic acids II into the salts or esters.

* * * * *

UNITED STATES PATENT AND TRADEMARK OFFICE
CERTIFICATE OF CORRECTION

PATENT NO. : 5,294,724

DATED : March 15, 1994

INVENTOR(S) : Heiner JENDRALLA et al.

It is certified that error appears in the above-indentified patent and that said Letters Patent is hereby corrected as shown below:

Claim 3, column 60, line 50, change "II/i" to --II/1--.

Delete the abstract in its entirety and substitute therefor: --4-Hydroxytetrahydropyran-2-ones of the Formula I and the corresponding dihydroxycarboxylic acid derivatives of the Formula II, their salts and esters, processes for their preparation, and their use as pharmaceuticals.

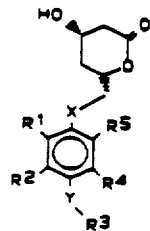

I

UNITED STATES PATENT AND TRADEMARK OFFICE
CERTIFICATE OF CORRECTION

PATENT NO. : 5,294,724  Page 2 of 2
DATED : March 15, 1994
INVENTOR(S) : Heiner Jendralla et al It is certified that error appears in the above-indentified patent and that said Letters Patent is hereby corrected as shown below:

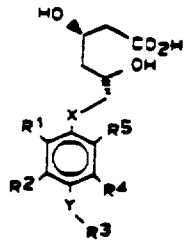

II

Signed and Sealed this

Twentieth Day of December, 1994

Attest:

BRUCE LEHMAN

Attesting Officer    Commissioner of Patents and Trademarks